United States Patent [19]

Fujie et al.

[11] Patent Number: 5,055,398

[45] Date of Patent: Oct. 8, 1991

[54] PROCESS FOR MEASURING THE CONCENTRATION OF A COMPONENT IN BODY FLUID SUCH AS URINE OR BLOOD

[75] Inventors: Shinichi Fujie, Saitama; Nobuo Oshima; Akira Matsuyuki, both of Tokyo, all of Japan

[73] Assignee: Kabushiki Kaisha Meidensha, Tokyo, Japan

[21] Appl. No.: 195,787

[22] Filed: May 19, 1988

[30] Foreign Application Priority Data

| May 22, 1987 | [JP] | Japan | 62-123952 |
| May 22, 1987 | [JP] | Japan | 62-123954 |
| May 22, 1987 | [JP] | Japan | 62-123957 |
| May 23, 1987 | [JP] | Japan | 62-125024 |
| May 23, 1987 | [JP] | Japan | 62-125025 |
| May 25, 1987 | [JP] | Japan | 62-125689 |
| Sep. 4, 1987 | [JP] | Japan | 62-220399 |
| Sep. 4, 1987 | [JP] | Japan | 62-220400 |

[51] Int. Cl.$^5$ .................... C12Q 1/26; C12Q 1/28; C12N 9/99
[52] U.S. Cl. ........................ 435/10; 435/25; 435/14; 435/28; 435/18; 435/27; 435/184; 436/174; 436/175; 436/178
[58] Field of Search .............. 435/25, 14, 28, 10, 435/18, 27, 184; 436/174, 175, 178

[56] References Cited

U.S. PATENT DOCUMENTS

| 4,172,765 | 10/1979 | Keyes | 435/14 |
| 4,242,446 | 12/1980 | Madappally et al. | 435/15 |
| 4,314,030 | 2/1982 | Habich | 435/296 |
| 4,416,982 | 11/1983 | Tsuda et al. | 435/11 |
| 4,550,078 | 10/1985 | Yamada et al. | 435/25 |
| 4,563,422 | 1/1986 | Deneke et al. | 435/27 |

*Primary Examiner*—Esther L. Kepplinger
*Assistant Examiner*—Toni Scheiner
*Attorney, Agent, or Firm*—Bachman & LaPointe

[57] ABSTRACT

A process for determining the concentration of a component, such as glucose, uric acid or polyamine, in a body fluid, such as urine, blood, blood serum, blood plasma, saliva or gastric juice, includes processing the body fluid with a catalase or an immobilized catalase for decomposing hydrogen peroxide included in the body fluid. When the body fluid is processed with the catalase, an inhibitor which inhibits the reaction between the catalase and the component is added to the body fluid after processing with the catalase. The process also includes processing the body fluid with a strongly basic anion exchange resin. When the concentration of polyamine in the body fluid is measured, the body fluid is processed with an acylpolyamineamido hydrolysis enzyme for converting acetylpolyamine into polyamine in the body fluid. After processing the body fluid by the these operations, hydrogen peroxide produced by the reaction between an oxidase and the component is measured.

18 Claims, 18 Drawing Sheets

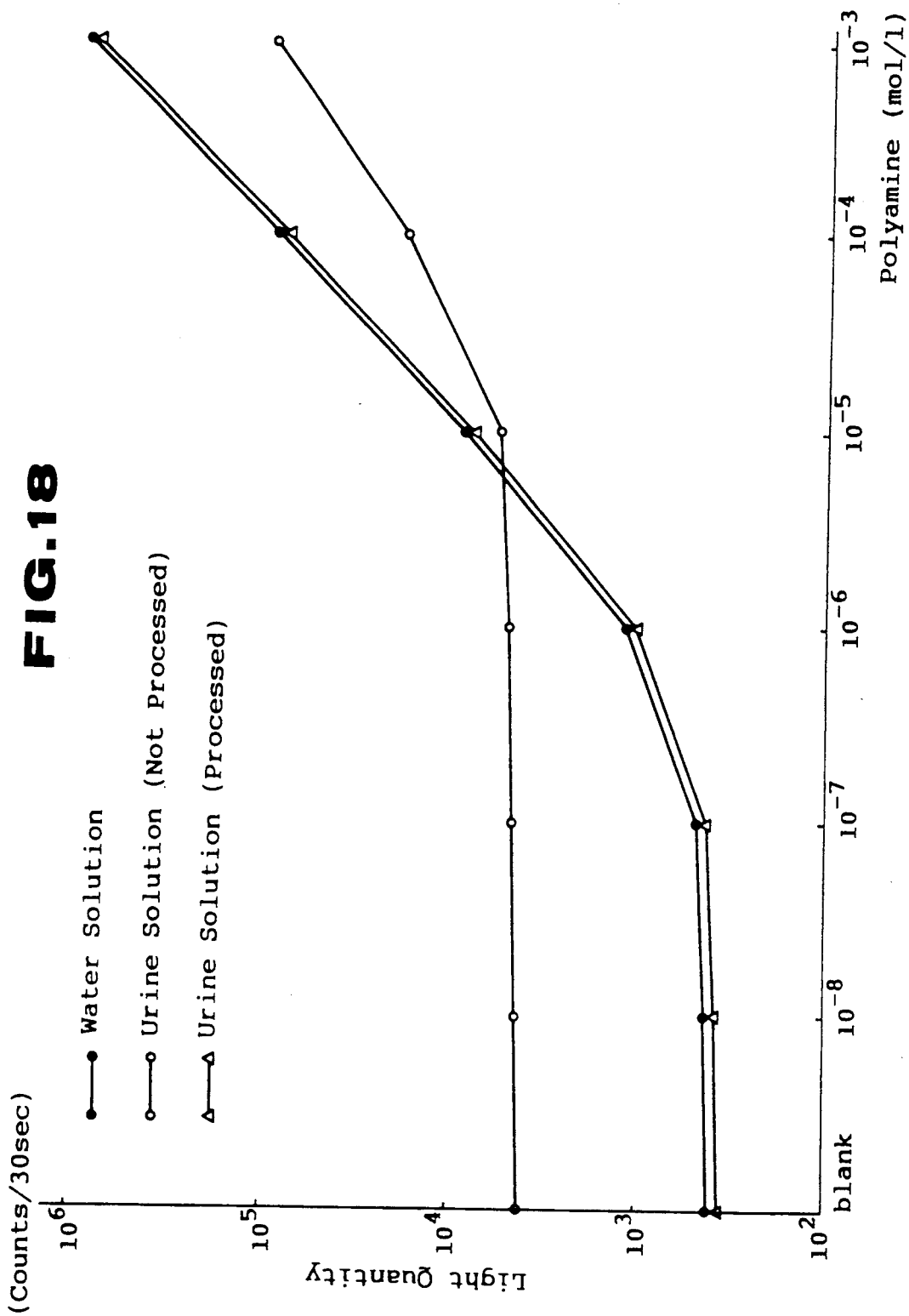

PROCESS FOR MEASURING THE CONCENTRATION OF A COMPONENT IN BODY FLUID SUCH AS URINE OR BLOOD

BACKGROUND OF THE INVENTION

1. Field of The Invention

The present invention relates generally to a process for measuring the concentration of a component in a body fluid, such as blood, urine or the like. More specifically, the invention relates to a process for measuring the concentration of a component, which is able to produce hydrogen peroxide in the presence of an oxidase, in a body fluid. Further specifically, the invention relates to a process for measuring the concentration of a component, such as glucose, uric acid or polyamine, which serves as a substrate for an oxidase to produce hydrogen peroxide in the present of the oxidase, in a body fluid.

2. Description of The Prior Art

As is well known, organic components, such as glucose, uric acid, polyamine or the like, exists in body fluids, such as urine, blood, blood serum, blood plasma, lymph, saliva, gastric juice or the like. In the case of healthy or normal organisms, the concentrations of these components are constant. On the other hand, in the case of an abnormal organism, they are changed. For the purpose of medical diagnosis, it is therefore very beneficial to be able to accurately determine the concentration of these components in body fluids.

In particular, a very small amount of glucose exists in body fluids, such as blood, urine or the like. In the case of healthy or normal organisms, the glucose in the body fluids exists exists in extremely small quantity. On the other hand, in the case of an abnormal organism, such as for example, a diabetic, the concentration of glucose increases markedly. For the purpose of medical diagnosis, it is therefore very beneficial to be able to determine the concentration of glucose in body fluids.

A process for determining the concentration of glucose by using the reducing power of glucose is known. In this process, complicated operations must be performed, and highly precise measurements can not be obtained since the specificity thereof is low.

In a recently developed process, the amount of hydrogen peroxide produced in a reaction between glucose and glucose oxidase is used to determine the glucose concentration. In this process, after glucose oxidase is added to a sample of a body fluid, the amount of hydrogen peroxide produced by the reaction between the glucose and glucose oxidase is determined by way of chemiluminescence method, and thereafter the concentration of glucose can be obtained from a previously made calibration curve representing the relationship between the glucose and hydrogen peroxide.

However, since normally a small amount of hydrogen peroxide already exists in body fluids, such as urine, it is difficult to accurately determine the concentration of glucose by determining that of hydrogen peroxide when the concentration of glucose in the urine is very small, i.e. less than $10^{-4}$ mol/l.

Furthermore, it is known that a small amount of uric acid also exists in body fluids, such as blood, urine or the like, and that the concentration of uric acid in blood decreases in the case of renoprival hypergia, gout, diabetes, carcinomatous neoplasm, eclampsia, incipient peripneumonia, enteropathy, metal intoxication, hypertension and so forth, and that the concentration of uric acid in urine increases in the case of leukosis, grave hepatopathy, gout and so forth. Accordingly, it is very beneficial to determine the concentration of uric acid in body fluids in diagnoses of the aforementioned diseases or the like. In clinical medicine, various methods have been used in order to determine the concentration of uric acid in blood and urine. However, in conventional methods, it is difficult to accurately, simply and promptly determine the concentration of uric acid.

In addition, a very small amount of polyamine also exists in urine. In healthy organisms, the polyamine concentration in the urine is extremely small. On the other hand, in the case of a cancer patient, the amount of polyamine increases markedly. It is therefore very beneficial, in diagnosing cancer patients and so forth, to determine the concentration of polyamine in urine.

In order to determine the concentration of polyamine in urine, electrophoresis method, thin-layar chromatography, analysis of amino acid, gas chromatography, high-speed fluid chromatography and so forth have been used. In these methods, there are problems in that complicated operations, and a long time for measurement and preprocessing are required, and many samples can not be measured at once.

In a recently developed method, after a deacetylation enzyme which can convert an acetylplyamine in urine into polyamine, the concentration of polyamine in the urine is measured by using a simple absorptiometry. However, this method is not simple, since centrifugation and other complicated operations in which, after polyamine is absorbed into a cation exchange resin, the resin is washed with water and a desorption solution to be neutralized are required, and a long time is also required for coloring.

It is therefore a principal object of the present invention to provide a process for simply and quickly measuring the concentration of a component in a body fluid, such as blood, urine or the like.

It is a particular object of the present invention to provide a process for accurately determining the concentration of a component, which produces hydrogen peroxide in the presence of an oxidase, in a body fluid.

It is another object of the present invention to provide a process for accurately determining the concentration of components, such as glucose, uric acid and polyamine, in a body fluid.

Further objects and advantage will appear hereinbelow.

SUMMARY OF THE INVENTION

In accordance with the present invention the foregoing objects and advantages are readily obtained.

According to one aspect of the present invention, a process for the determination of the concentration of a component, which selectively reacts with an oxidase to produce hydrogen peroxide, in a body fluid comprises the steps of:

providing a body fluid;

mixing the body fluid with a catalase for decomposing the hydrogen peroxide in the body fluid;

adding an inhibitor, which inhibits a reaction between catalase and hydrogen peroxide, to the mixture of the catalase and the body fluid;

processing the mixture with the oxidase for producing hydrogen peroxide;

measuring the concentration of hydrogen peroxide produced by the reaction between the oxidase and the component; and determining the concentration of the component from the measured concentration of the hydrogen peroxide.

The process may further include processing the body fluid with an anion exchange resin. The anion exchange resin is preferably a strongly basic anion exchange resin. The inhibitor may be selected from the group consisting of sodium azide, hydrogen cyanide, hydrogen sulfide, ammonium hydroxide, and 3-amino-1,2,4-triazole. The body fluid may be selected from the group consisting of urine, blood, blood serum, blood plasma, saliva, lymph and gastric juice. The component may serve as a substrate for the oxidase to produce hydrogen peroxide in the presence of the oxidase, and it is preferably selected from the group consisting of glucose, uric acid and polyamine. In the case of the component is glucose, the oxidase is glucose oxidase. In the case of the component is uric acid, the oxidase is uricase. In the case of the component is polyamine, the oxidase is putrescene oxidase. When the concentration of polyamine is measured, the process may further include processing the body fluid with a deacetylating enzyme for converting acetylpolyamine included in the body fluid into polyamine. The deacetylating enzyme is preferably acylpolyamineamido hydrolysis enzyme.

According to another aspect of the invention, a process for the determination of the concentration of a component, which selectively reacts with an oxidase to produce hydrogen peroxide, in a body fluid comprises the steps of:

providing a body fluid;

bringing the body fluid into contact with an immobilized catalase to decompose the hydrogen peroxide in the body fluid;

processing the body fluid with the oxidase for producing hydrogen peroxide;

measuring the concentration of the hydrogen peroxide produced by the reaction between the oxidase and the component; and determining the concentration of the component from the measured concentration of hydrogen peroxide.

The process may further include processing the body fluid with an anion exchange resin. The anion exchange resin is a strongly basic anion exchange resin. The body fluid may be selected from the group consisting of urine, blood, blood serum, blood plasma, saliva, lymph and gastric juice. The component may serve as a substrate for the oxidase to produce hydrogen peroxide in the presence of the oxidase, and it is preferably selected from the group consisting of glucose, uric acid and polyamine. In cases where the component is glucose, the oxidase is glucose oxidase. In cases where the component is uric acid, the oxidase is uricase. In cases where the component is polyamine, the oxidase is putrescene oxidase. In this case, the process may further include processing the body fluid with a deacetylating enzyme for converting acetylpolyamine included in the body fluid into polyamine. The deacetylating enzyme is preferably acylpolyamineamido hydrolysis enzyme.

According to another aspect of the invention, a process for the determination of the concentration of a component, which selectively reacts with an oxidase to produce hydrogen peroxide, in a body fluid comprising the steps of:

providing a body fluid;

processing the body fluid with an enzyme which decomposes hydrogen peroxide, for decomposing the hydrogen peroxide therein;

processing the body fluid with said oxidase for producing hydrogen peroxide;

measuring the concentration of the hydrogen peroxide produced by the reaction between the oxidase and the component; and determining the concentration of the component from the measured concentration of hydrogen peroxide.

BRIEF DESCRIPTION OF THE DRAWINGS

The present invention will be understood more fully from the accompanying drawings of the preferred embodiments of the invention. The drawings are not intended to imply limitation of the invention to these specific embodiments, but are for explanation and understanding only.

In the drawings:

FIG. 18 is a graph illustrating the quantity of light produced versus the concentration of polyamine in Example VIII.

DESCRIPTION OF THE PREFERRED EMBODIMENT

Figure 1:
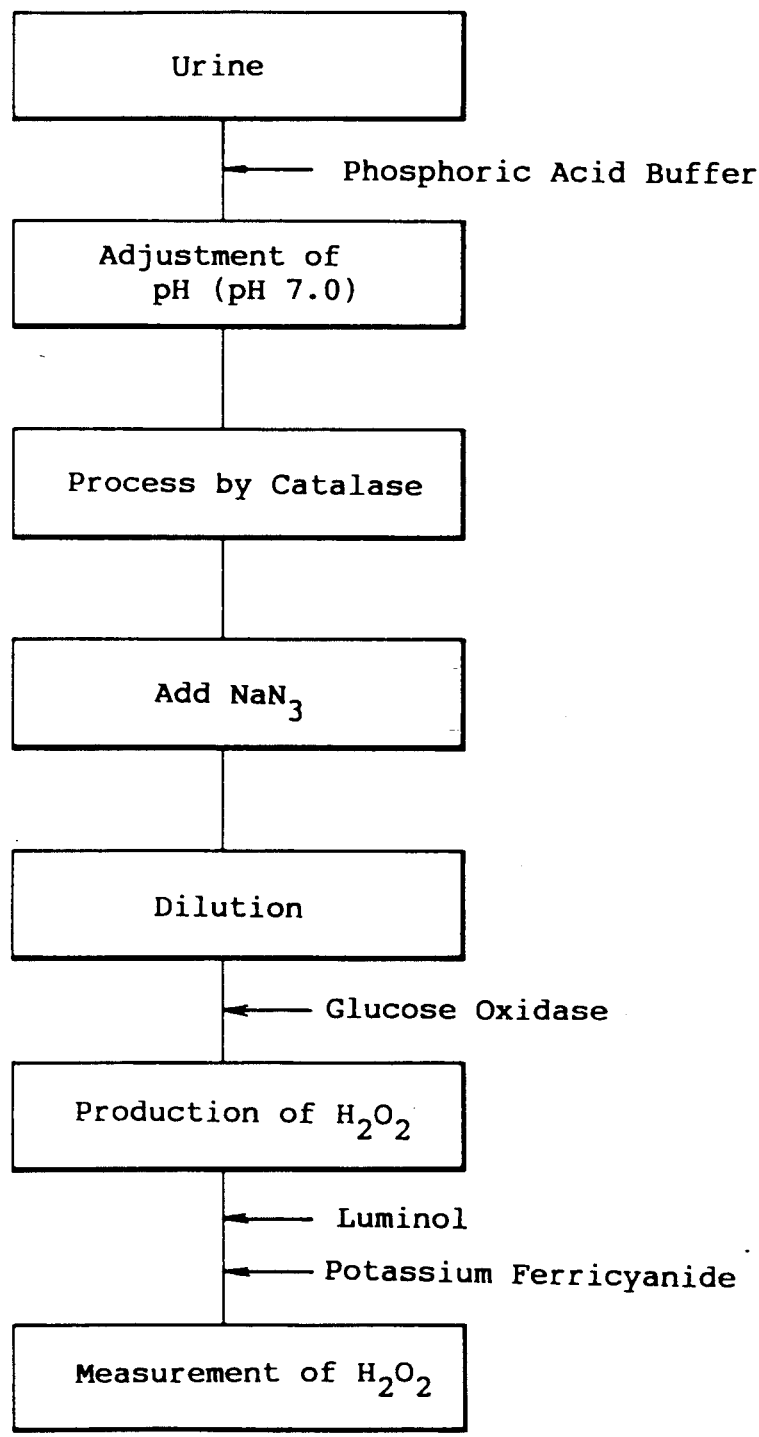
FIG. 1 is a flow chart of operations of Example I according to the present invention.

In accordance with the present invention, the process for measuring the concentration of a component, which selectively reacts with an oxidase to produce hydrogen peroxide, in a body fluid comprises the steps of: providing a sample of the body fluid; mixing the sample of the body fluid with a catalase for decomposing the hydrogen peroxide in the body fluid; adding an inhibitor, which inhibits a reaction between catalase and hydrogen peroxide, to the mixture of the catalase and the body fluid; processing the mixture with the oxidase for producing hydrogen peroxide; measuring the concentration of the hydrogen peroxide produced by the reaction between the oxidase and the component; and determining the concentration of the component from the measured concentration of the hydrogen peroxide.

In accordance with the present invention, hydrogen peroxide included in the body fluid can be removed by processing the body fluid with the catalase, so that the concentration of hydrogen peroxide produced by the reaction between the oxidase and the component in the body fluid can be accurately measured. The concentration of the component in the body fluid can be easily obtained from a calibration curve illustrating the relationship between the concentrations of hydrogen peroxide and the component. By this process, relatively low concentrations, such as less than $10^{-4}$ mol/liter, of the component in the body fluid can be accurately determined. In accordance with the present invention, the body fluid may be processed with an anion exchange resin, such as strongly basic anion exchange resin. By this process, materials formed by metabolism in the body fluid can be removed, so that the concentration of the component can be accurately determined when the concentration thereof is relatively high, such as greater than $10^{-4}$ mol/liter.

In accordance with the present invention, the inhibitor may be selected from the group consisting of sodium azide, hydrogen cyanide, hydrogen sulfide, ammonium hydroxide, and 1-amino 1,2,4-triazole. By experiment, it was confirmed that, when any one of these materials was used as the inhibitor, similar results could be obtained. According to the process of the invention, the concentration of a component, such as glucose, uric acid, polyamine or the like, in a body fluid, such as urine, blood, blood serum, blood plasma, saliva, lymph or gastric juice may be determined. When the concentration of glucose is to be determined, glucose oxidase is used as the oxidase. When the concentration of uric acid is to be determined, uricase is used as the oxidase. When the concentration of polyamine is to be determined, putrescene oxidase is used as the oxidase. When the concentration of polyamine is to be determined, the body fluid is preferably processed with a deacetylating enzyme, such as an acylpolyamineamido hydrolysis enzyme, for converting acetylpolyamine included in the body fluid into polyamine.

In cases where the concentration of hydrogen peroxide produced by the reaction between the oxidase and the component is measured by way of chemiluminescent method, a luminescent reagent, such as luminol, and a catalyst, such as potassium ferricyanide, are added to the body fluid sample processed by the aforementioned operations. Light produced by the reaction the luminescent material and the component in the body fluid in the presence of the catalyst may be measured by a luminometer. When the luminescent material and the calayst are previously processed by a catalase or an immobilized catalase, the concentration of the component can be more accurately determined. In order to measure the concentration of hydrogen peroxide, various methods, such as laser turvidimetric analysis, polarography, permanganate method, iodic acid reductometry, can be used. By experiment, it was confirmed that, when any one of these methods was used, similar results could be obtained.

In accordance with the present invention, the process for measuring the concentration of a component, which selectively reacts with an oxidase to produce hydrogen peroxide, in a body fluid comprises the steps of: providing a sample of the body fluid; bringing the body fluid sample into contact with an immobilized catalase to decompose the hydrogen peroxide in the body fluid; processing the body fluid with an oxidase for producing hydrogen peroxide; measuring the concentration of the hydrogen peroxide produced by the reaction between the oxidase and the component; and determining the concentration of the component from the measured concentration of hydrogen peroxide.

According to this process, it is not required to use an inhibitor. Therefore, the determination of the concentration of the component in the body fluid can be made simpler by prepreparing an immobilized catalase.

The effectiveness of the present invention is illustrated by the following examples.

EXAMPLE I

Assuming that the amount of glucose in the urine of a healthy person is essentially zero, eight urine solutions containing 0, $10^{-5}$, $10^{-4}$, $10^{-3}$, $10^{-2}$, $10^{-1}$ and 10 mol/liter glucose were prepared by adding glucose to urine. Using the respective urine solutions, the following experiment was performed.

After the pH of the urine solution was measured, 1 mililiter of a buffer solution containing a 0.1 mol/liter phosphoric acid (pH 5.0 to 8.0) was added to 1 mililiter of the urine solution, so that the pH of the urine solution was adjusted to be 7.0. Thereafter, 0.01 mililiter of a solution containing a 10,000 U/mililiter catalase, which was formed by diluting 42,500 U/mililiter catalase solution (made by SIGMA CHEMICAL Co.,Ltd from Bovine Liver) with a buffer solution containing a 0.01 mol/liter phosphoric acid (pH 7.0), was added to 1 mililiter of the adjusted urine, and warmed in a 30° C. water bath for ten minutes. Thereafter, the urine solution was taken out of the water bath, and 0.01 mililiter of a water solution containing 1 mol/liter sodium azide ($NaN_3$) (made by Kokusan Chemical Works Ltd.) serving as an inhibitor, for inhibiting the reaction between the catalase and hydrogen peroxide in the urine, was added to the urine solution. Then, 0.2 mililiters of this solution was diluted with 9.8 mililiters of water.

By the aforementioned operations, processed urine solutions essentially containing 0, $10^{-7}$, $10^{-6}$, $10^{-5}$, $10^{-4}$, $10^{-3}$, $10^{-2}$ and $10^{-1}$ mol/liter glucose were prepared. Then, 0.01 mililiter of a solution containing a 100 U/mililiter glucose oxidase, which was formed by diluting glucose oxidase (made by TOYOBO Co.,Ltd. from Aspergillus niger) with a buffer solution (pH 5.1) containing a 0.01 mol/liter acetic acid, was added to the respective processed urine solutions, so that hydrogen peroxide was produced by the respective enzyme reactions.

Thereafter, 0.5 mililiters of an aqueous solution containing a $2 \times 10^{-7}$ mol/liter luminol serving as a luminescent reagent, which was formed by diluting luminol (made by MERCK Co. Ltd. pro analysi) with a buffer solution containing 0.2 mol/liter sodium carbonate and sodium hydrogencarbonate, and 0.5 mililiters of an aqueous solution containing a $6 \times 10^{-3}$ mol/liter potassium ferricyanide (made by TOKYO KASEI KOGYO Co.,Ltd.) were added to the the respective solutions. The quantity of light produced by the reaction between the luminol and the hydrogen peroxide in the presence of the potassium ferricyanide was measured by a luminometer (UPD-8000 made by KABUSHIKI KAISHA MEIDENSHA).

For reference, eight water solutions containing 0 and $10^{-7}$ to $10^{-1}$ mol/liter glucose, and eight urine solutions containing 0, $10^{-7}$ to $10^{-1}$ mol/liter glucose, which were not processed by the catalase, were prepared. With respect to these solutions, the quantity of light produced by each of the respective reactions was measured in a similar manner to Example I.

Figure 2:
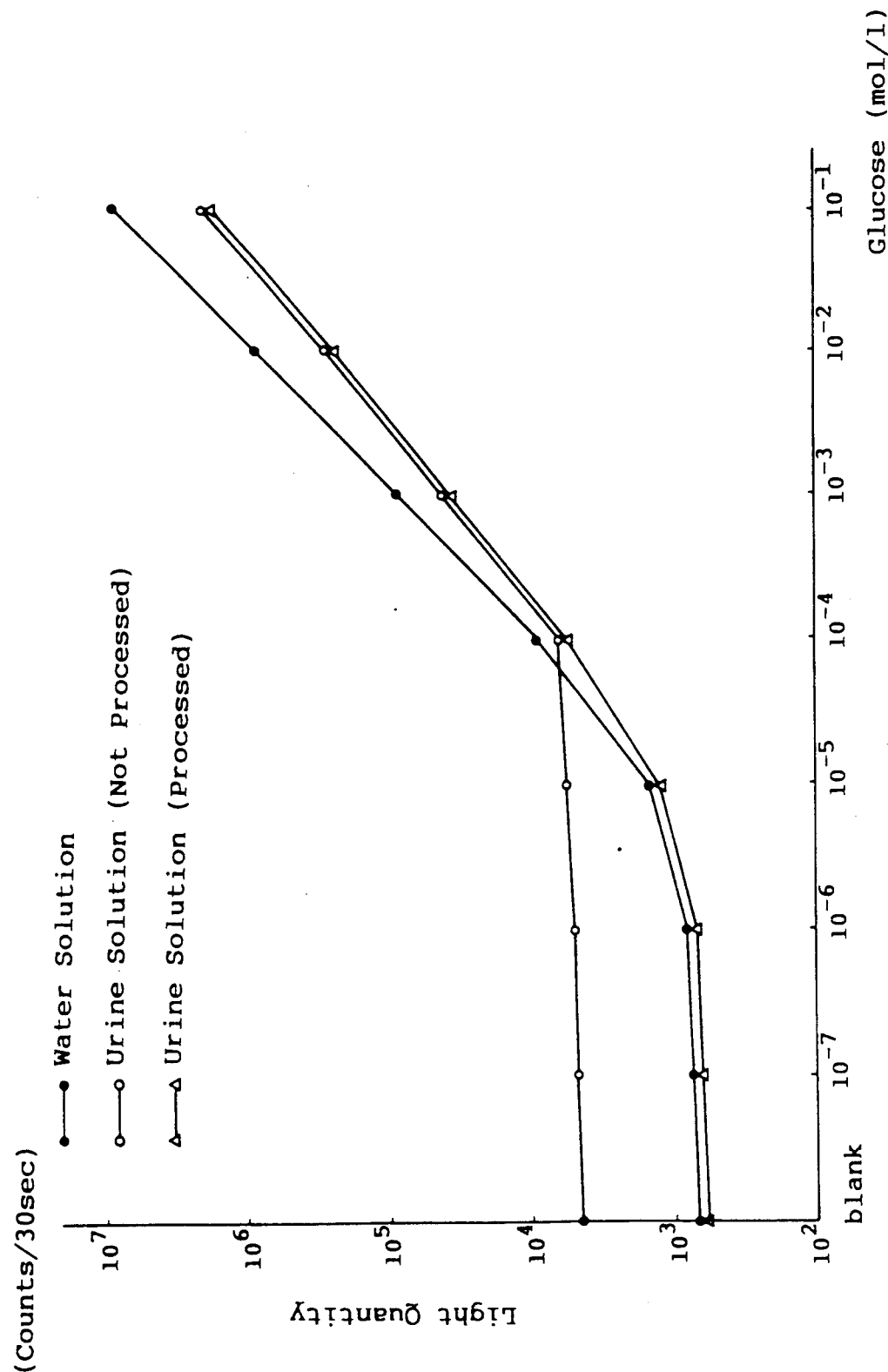
FIG. 2 is a graph illustrating the quantity of light produced versus the concentration of glucose in Example I.

FIG. 1 is a flow chart of the aforementioned operation, and FIG. 2 shows the relationship between the concentration of glucose and the quantity of light produced by each of the respective reactions.

As shown in FIG. 2, in the case of urine solutions which were not processed by the catalase, the proportion of the hydrogen peroxide included in the initial urine to the hydrogen peroxide produced by the reaction between the glucose and the glucose oxidase is relatively high when the concentration of the glucose is relatively low, such as less than $10^{-4}$ mol/liter. As a result, the measured quantity of emitted light is much greater than that of light produced by the reaction with the hydrogen peroxide produced by the enzyme reaction. That is, the background light greatly affected the measured value when the concentration of glucose was less than $10^{-4}$ mol/liter, so that it was difficult to accurately measure the concentration of glucose when it was so low. On the other hand, in the case of Example I, the background light hardly affected the measured value when the concentration of glucose was about $10^{-7}$ mol/liter. Therefore, it was found that low concentrations of glucose, up to about $10^{-7}$ mol/liter, can be accurately measured in accordance with the method of the present invention.

As shown in FIG. 2, when the concentration of glucose is greater than $10^{-4}$ mol/liter, the quantity of light of Example I is less than that of the water solution. The difference therebetween can be corrected by Example II which will be described below.

EXAMPLE II

Urine solutions containing 0, $2 \times 10^{-6}$, $2 \times 10^{-5}$, $2 \times 10^{-4}$, $2 \times 10^{-3}$, $2 \times 10^{-2}$, $2 \times 10^{-1}$ and 2 mol/liter glucose were prepared by adding glucose to urine of a healthy person. Using the respective urine solutions, the following experiment was performed.

2 mililiters of strongly basic anion exchange resin ($OH^-$-type), formed by converting $Cl^-$-type anion exchange resin (AG1-X4 made by BIO-RAD Laboratories, with grain size of 100 to 200 mesh) into $OH^-$-type by 1N sodium hydroxide, was added to 2 mililiters of the urine solution, and was stirred. Then, the supernatant solution was collected, and 1 mililiter of a buffer solution (pH 6.0) containing a 0.1 mol/liter phosphoric acid was added to the supernatant solution so that the pH thereof was adjusted to be 7.0. Then, 0.01 mililiter of the 10,000 U/mililiter catalase solution prepared in Example I was added to the supernatant solution, and allowed to warm in a water bath at 30° C. for ten minutes. After taking it out of the water bath, 0.01 mililiter of a water solution containing 1 mol/liter sodium azide serving as the inhibitor was added the reaction solution. Then. 0.2 mililiters of this solution was diluted with 0.8 mililiters of water.

By the aforementioned operations, processed urine solutions essentially containing 0, $10^{-7}$, $10^{-6}$, $10^{-5}$, $10^{-4}$, $10^{-3}$, $10^{-2}$ and $10^{-1}$ mol/liter glucose were produced. Then, 0.01 mililiter of the 100 U/mililiter glucose oxidase prepared in Example I was added to the respective processed solutions, so as to cause hydrogen peroxide to be produced by the enzyme reaction.

Thereafter, 0.5 mililiters of the $2 \times 10^{-7}$ mol/liter luminol solution and 0.5 mililiters of the $6 \times 10^{-3}$ mol/liter potassium ferricyanide solution, which were prepared in Example I, were added to the respective solutions. The quantity of light produced by each of the reactions between the luminol and the hydrogen peroxide in the presence of the potassium ferricyanide was measured by the luminometer.

For reference, eitht water solutions containing 0 and $10^{-7}$ to $10^{-1}$ mol/liter glucose, and eight urine solutions containing 0 and $10^{-7}$ to $10^{-1}$ mol/liter glucose, which were not processed by the catalase and the anion exchange resin, were prepared, and the quantity of light produced by each of the respective reactions was measured in a similar manner to Example II.

Figure 3:
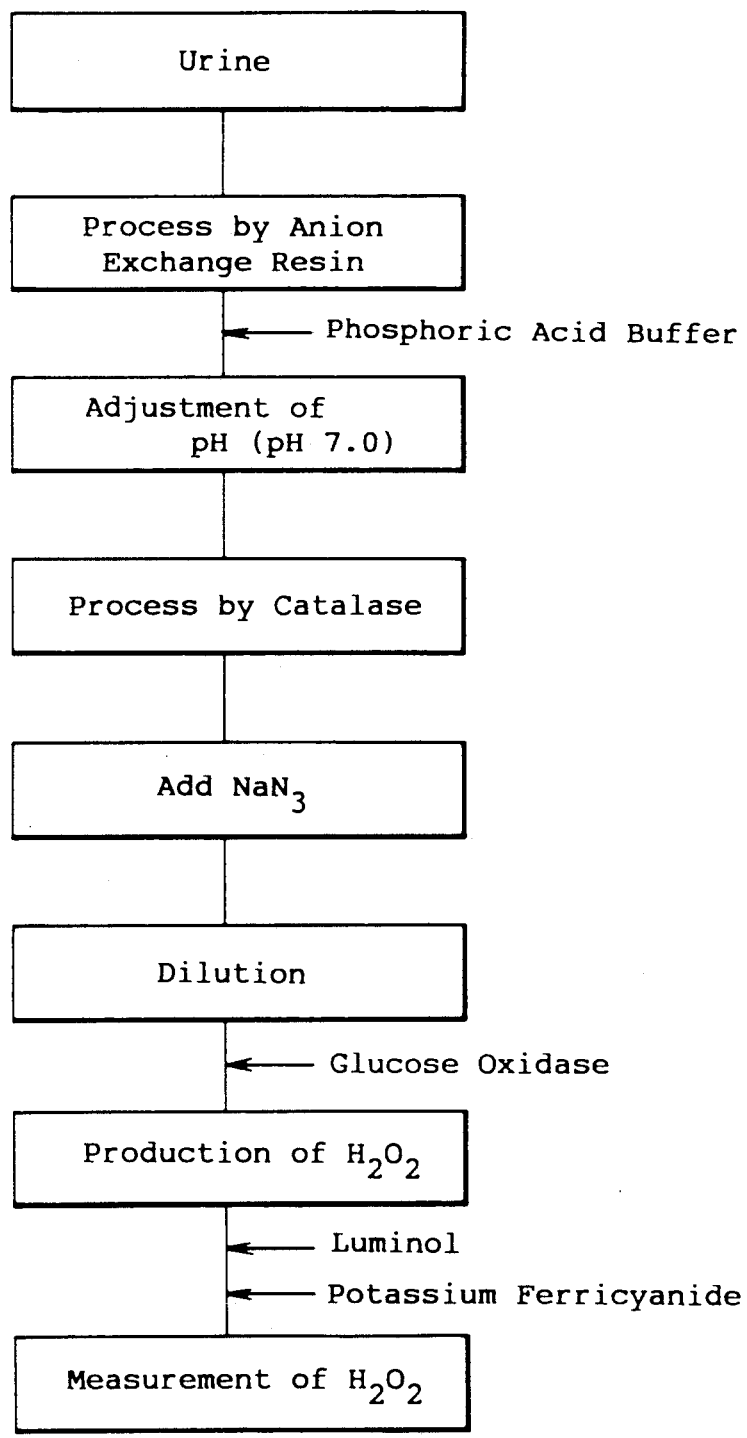
FIG. 3 is a flow chart of operations of Example II according to the present invention.
Figure 4:
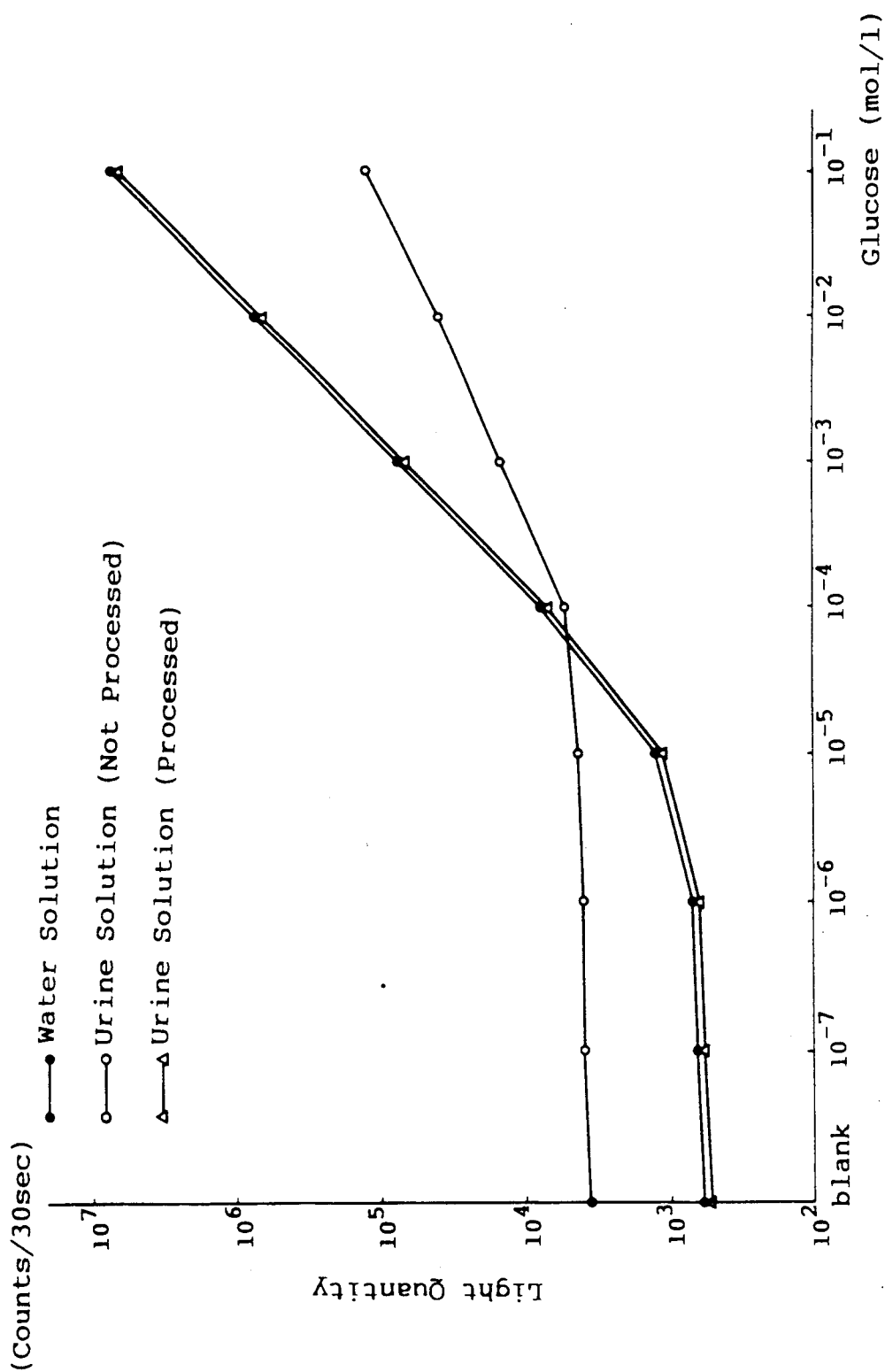
FIG. 4 is a graph illustrating the quantity of light produced versus the concentration of glucose in Example II.

FIG. 3 shows a flow chart of the aforementioned operation, and FIG. 4 shows the relationship between the concentration of glucose and the quantity of light produced by each of the respective reactions.

As shown in FIG. 4, the difference between the quantity of light of Example II and that of the water solution was very small when the conentration of glucose was greater than $10^{-4}$ mol/liter, indicating that the concentration of glucose can be accurately measured in accordance with the present invention.

EXAMPLE III

A polyfunctional reagent was caused to react with water insoluble carrier, and thereafter a catalase was attached thereto so as to immobilize the catalase. An aminopropyl-CPG (controlled pore glass) (made by ELECTRO-NUCLEONICS INC.; with 120 to 200 mesh of pore diameter) and a glutaraldehyde were used as the water insoluble carrier and the polyfunctional reagent, respectively. Specifically, 1 gram of the aminopropyl-CPG was immersed in 25 mililiters of a buffer solution containing 2.5 % glutaraldehyde and 0.01% phosphric acid for two hours at room temperature to form an aldehyde CPG. Thereafter, the aldehyde CPG was caused to react with 2 mililiters of a buffer solution containing 100,000 U/mililiter catalase and 0.01% phosphoric acid for three hours at room temperature to produce an immobilized catalase.

This reaction can be expressed by the following formulae.

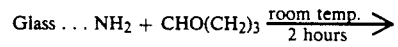

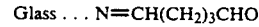

-continued

Glass ... $N=CH(CH_2)_3CH=NR$

Then, urine solutions containing 0, $2\times10^{-6}$, $2\times10^{-5}$, $2\times10^{-4}$, $2\times10^{-3}$, $2\times10^{-2}$, $2\times10^{-1}$ and 2 mol/liter glucose were prepared by adding glucose to urine. Using the respective urine solutions, the following experiment was performed.

After the pH of the urine solution was measured, 1 mililiter of a buffer solution containing a 0.1 mol/liter phosphoric acid (pH 5.0 to 8.0) was added to 1 mililiter of the urine solution, so that the pH of the urine solution was adjusted to be 7.0. Then, 2 mililiters of the adjusted urine was caused to pass through a column in which the aforementioned immobilized catalase was packed. The initial 0.5 mililiters of the filtrate was discarded and next filtrate was collected. Then, 0.2 mililiters of this filtrate was diluted with 9.8 mililiters of water.

By the aforementioned operation, processed urine solutions essentially containing 0, $10^{-7}$, $10^{-6}$, $10^{-5}$, $10^{-4}$, $10^{-3}$, $10^{-2}$ and $10^{-1}$ mol/liter glucose were prepared. Then, 0.01 mililiter of the 100 U/mililiter glucose oxidase solution prepared in Example I was added to the respective processed urine solutions so as to cause hydrogen peroxide to be produced.

Thereafter, 0.5 mililiters of the $2\times10^{-7}$ mol/liter luminol solution and 0.5 mililiters of the $6\times10^{-3}$ mol/liter potassium ferricyanide solution, which were prepared in Example I, were added to the respective solutions. The quantity of light produced by each of the reactions between the luminol and the hydrogen peroxide in the presence of the potassium ferricyanide was measured by the luminometer.

In order to compare with Example III, water solutions containing 0 and $10^{-7}$ to $10^{-1}$ mol/liter glucose and urine solutions containing 0 and $10^{-7}$ to $10^{-1}$ mol/liter glucose, which were not processed by the immobilized catalase. With respect to these solutions, the quantity of light produced by each of the respective reactions was measured in a similar manner to Example III.

Figure 5:
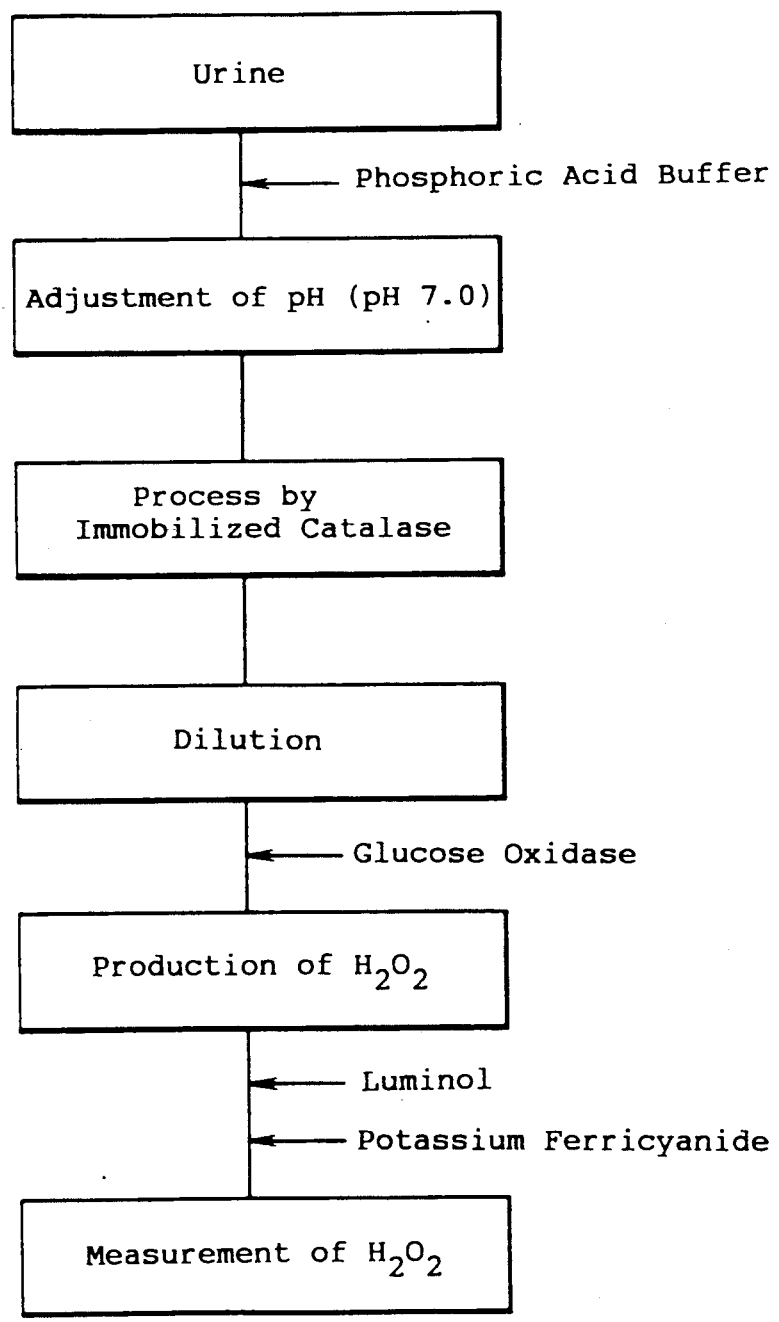
FIG. 5 is a flow chart of operations of Example III according to the present invention.
Figure 6:
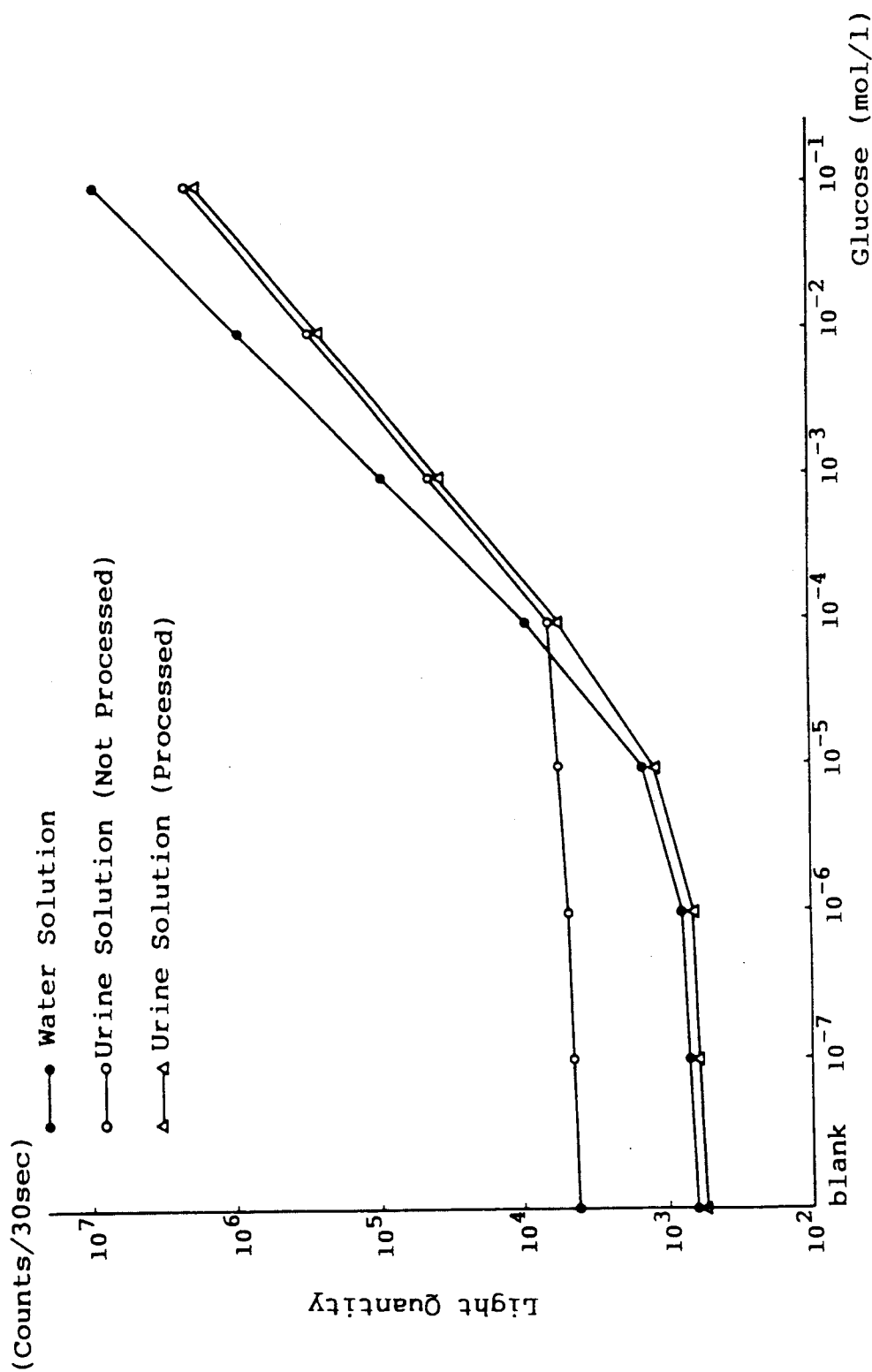
FIG. 6 is a graph illustrating the quantity of light produced versus the concentration of glucose in Example III.

These operations and their results are shown in FIGS. 5 and 6.

As seen from FIG. 6, in the case of Example III, similar results to Example I were obtained. With this process, it is not required to use an inhibitor to inhibit the reaction between the catalase and the hydrogen peroxide, which makes the operation simpler than that of Example I if the column in which the immobilized catalase is packed is previously prepared.

Similar to Example I, in Example III, when the concentration of glucose is greater than $10^{-4}$ mol/liter, the quantity of light emitted is less than that of the water solution. In Example IV which will be described below, the difference therebetween can be corrected.

EXAMPLE IV

Urine solutions containing 0, $2\times10^{-6}$, $2\times10^{-5}$, $2\times10^{-4}$, $2\times10^{-3}$, $2\times10^{-2}$, $2\times10^{-1}$ and 2 mol/liter glucose were prepared by adding glucose to normal urine. Using the respective urine solutions, the following experiment was performed.

2 mililiters of strongly basic anion exchange resin similar to that of Example II was added to 2 mililiters of urine solution, and was stirred. Then, the supernatant solution was collected, and 1 mililiter of a buffer solution (pH 6.0) containing a 0.1 mol/liter phosphric acid was added to the supernatant solution so that the pH thereof was adjusted to be 7.0. Then, 2 mililiters of the adjusted urine solution was caused to pass through the columun in which the immobilized catalase prepared in Example III was packed. The initial 0.5 mililiters of the filtrate was discarded whereafter the filtrate was collected. Then, 0.2 mililiters of this filtrate was diluted with 9.8 mililiters of water.

By the aforementioned operations, processed urine solutions essentially containing 0, $10^{-7}$, $10^{-6}$, $10^{-5}$, $10^{-4}$, $10^{-3}$, $10^{-2}$ and $10^{-1}$ mol/liter glucose were prepared. Then, 0.01 mililiter of the 100 U/mililiter glucose oxidase solution prepared in Example I was added to the respective processed urine solutions so as to cause hydrogen peroxide to be produced.

Thereafter, 0.5 mililiters of the $2\times10^{-7}$ mol/liter luminol solution and 0.5 mililiters of the $6\times10^{-3}$ mol/liter potassium ferricyanide solution, which were prepared in Example I, were added to the respective solutions. The quantity of light produced by the reaction between the luminol and the hydrogen peroxide in the presence of the potassium ferricyanide in each of the solutions was measured by luminometer.

In order to compare with Example IV, water solutions containing 0 and $10^{-7}$ to $10^{-1}$ mol/liter glucose, and urine solutions containing 0 and $10^{-7}$ to $10^{-1}$ mol/liter glucose, which were not processed by the immobilized catalase and the anion exchange resin, were prepared. The quantity of light produced by the reaction in each of the solutions was measured in a similar manner to Example VI.

Figure 7:
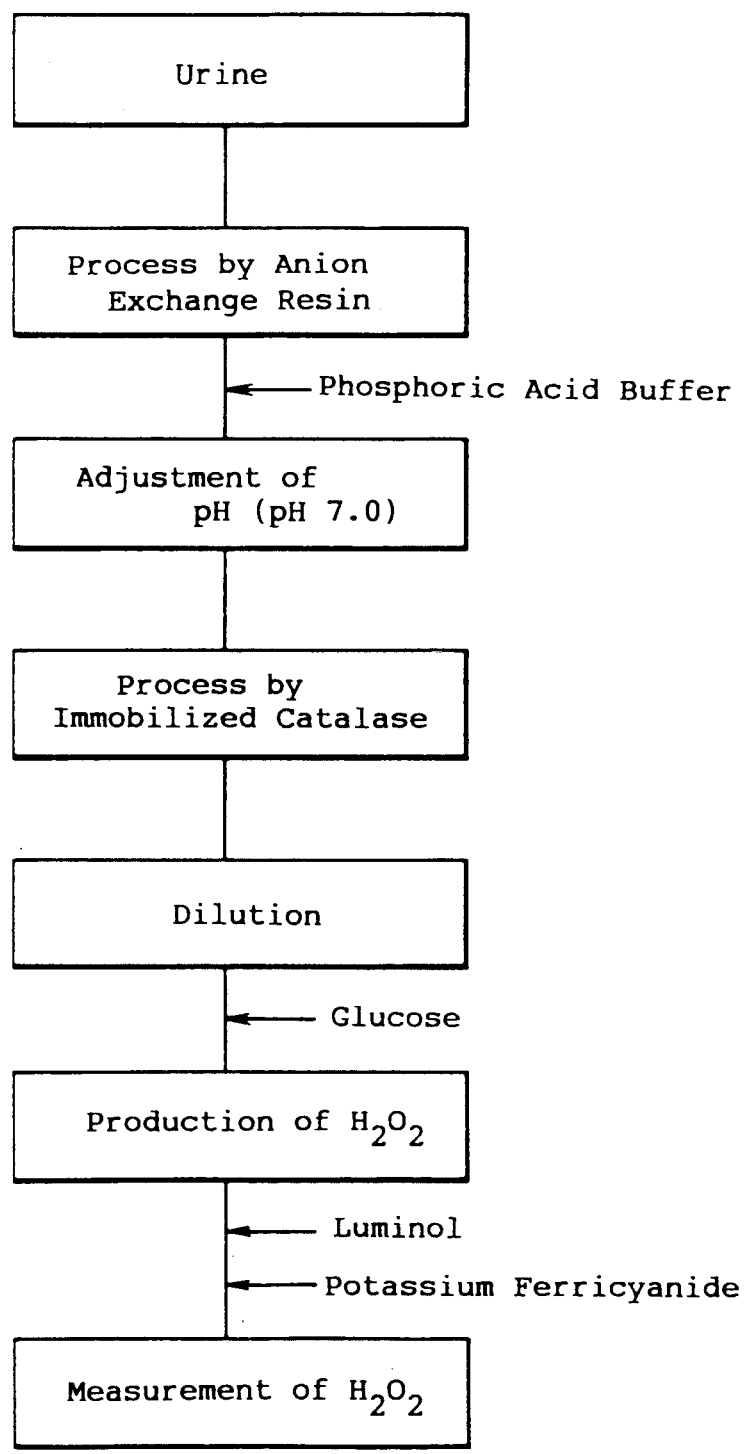
FIG. 7 is a flow chart of operations of Example IV according to the present invention.
Figure 8:
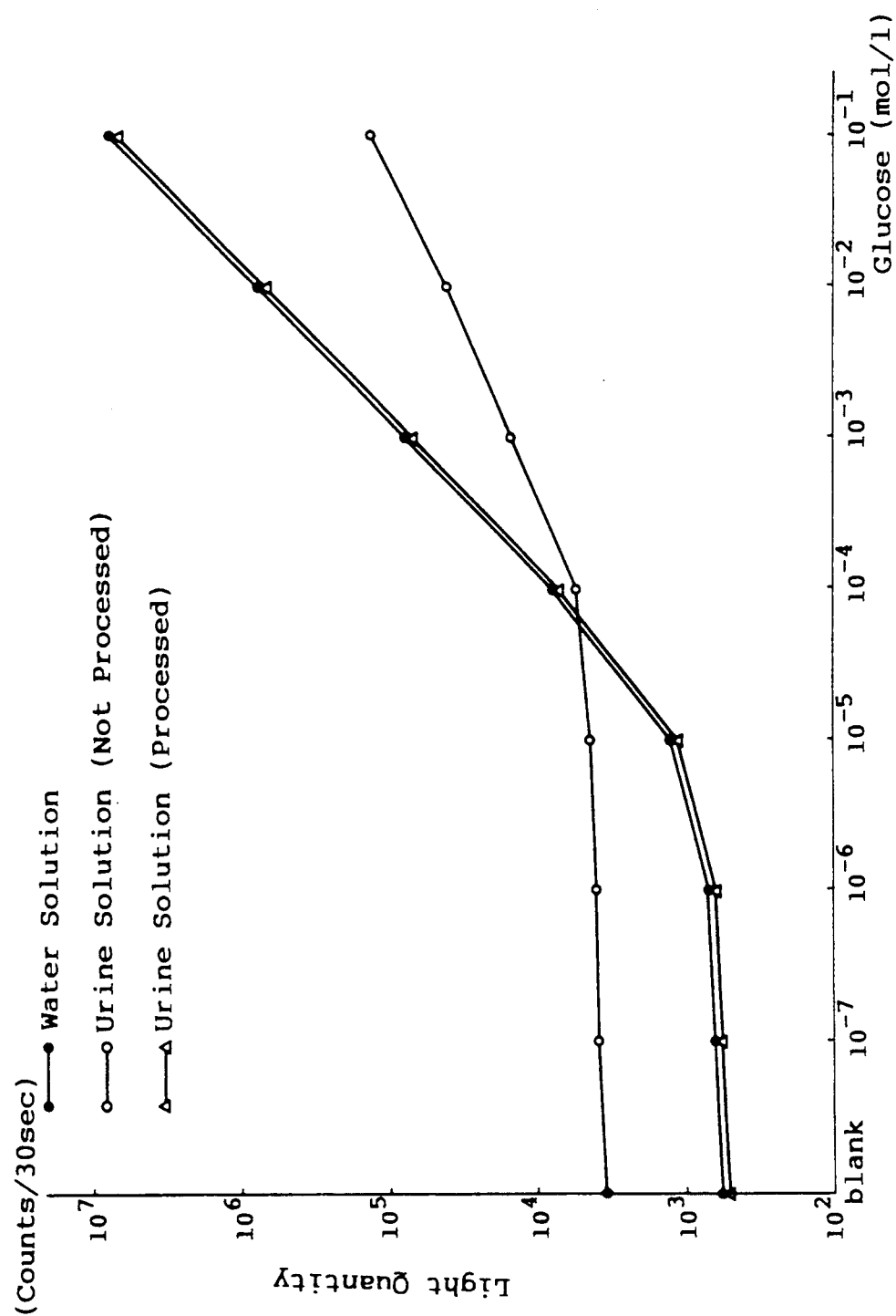
FIG. 8 is a graph illustrating the quantity of light produced versus the concentration of glucose in Example IV.

These operations and results are shown in FIGS. 7 and 8.

As seen from FIG. 8, in the case of Example IV, similar results to Example II were obtained. In accordance with this process, the concentration of glucose can be accurately measured without using the inhibitor used in Example II.

EXAMPLE V

Assuming that the amount of uric acid in the urine of a healthy person is essentially zero, an initial urine solution containing 5.9 miligram/deciliter uric acid was prepared by adding uric acid to urine. Using this initial solution, four urine solutions were prepared in which the initial solution was undiluted, diluted with urine by a quarter, a half and three quarters.

Then, an equal volume of a buffer solution containing a 0.1 mol/liter of phosphoric acid was added to each of urine solutions, and the pH of each of the solutions was adjusted to be 7.0. Then, 0.01 mililiter of a 10,000 catalase solution as prepared in Example 1 was added to each of 1 mililiter of these solutions by means of a pipette, and the reaction therebetween was allowed to occur at 30° C. for ten minutes, so that hydrogen peroxide in the solution was decomposed. Thereafter, in order to inhibit the reaction between the catalase and the hydrogen peroxide, 0.01 mililiter of water solution containing 1 mol/liter sodium axide serving as an inhibitor was added to each of the aforementioned solutions by means of a pipette. To one part by volume of the respective solutions were then added 99 parts by volume of distilled water, and thereafter 0.01 mililiter of uricase solution, which was prepared by dissolving uricase (made by Boeringer Mnnheim Co., Ltd.; with 50% glycerin; Sp. activity of 4.5 U/miligram (25° C.)) with a 0.13 mol/liter sodium carbonate (pH 10.2), was added to 1 mililiter of each of the diluted solutions by pipette, and allowed to react at 30° C. for ten minutes, and thereby producing hydrogen peroxide.

This reaction can be expressed by the following formula:

After the reaction, 0.5 mililiters of the $2 \times 10^{-7}$ mol/liter luminol solution and 0.5 mililiters of the $6 \times 10^{-3}$ mol/liter potassium ferricyanide solution, which were prepared in Example I, were added to the respective solutions. The quantity of light produced by the reaction between the luminol and the hydrogen peroxide in the presence of the potassium ferricyanide in the respective solutions was measured by luminometer.

For reference, water solutions containing 5, 10 and 14 miligram/deciliter uric acid were prepared. The quantity of light produced by each of the respective reactions was measured in a similar manner to Example V.

Figure 9:
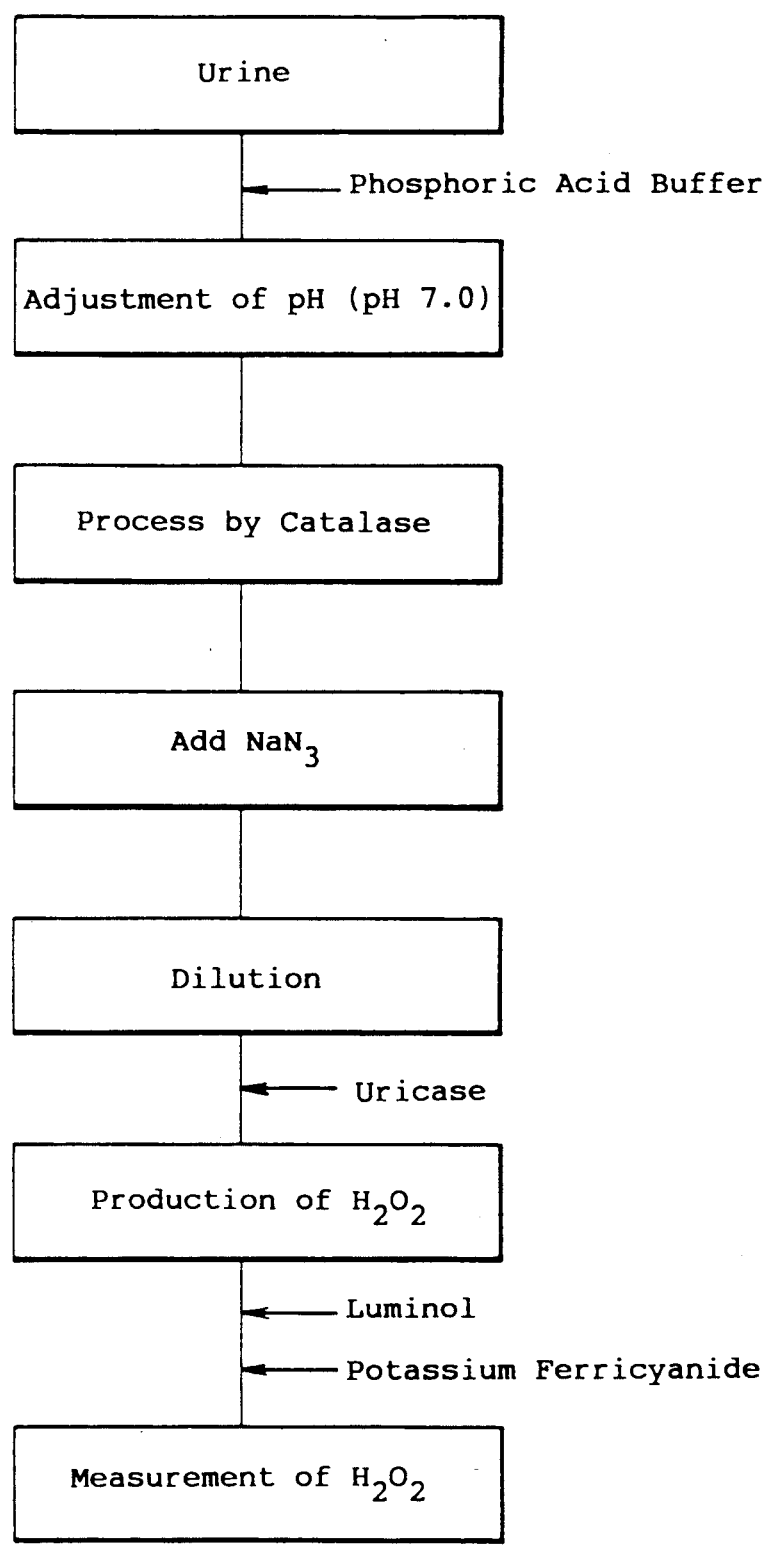
FIG. 9 is a flow chart of operations of Example V according to the present invention.
Figure 10:
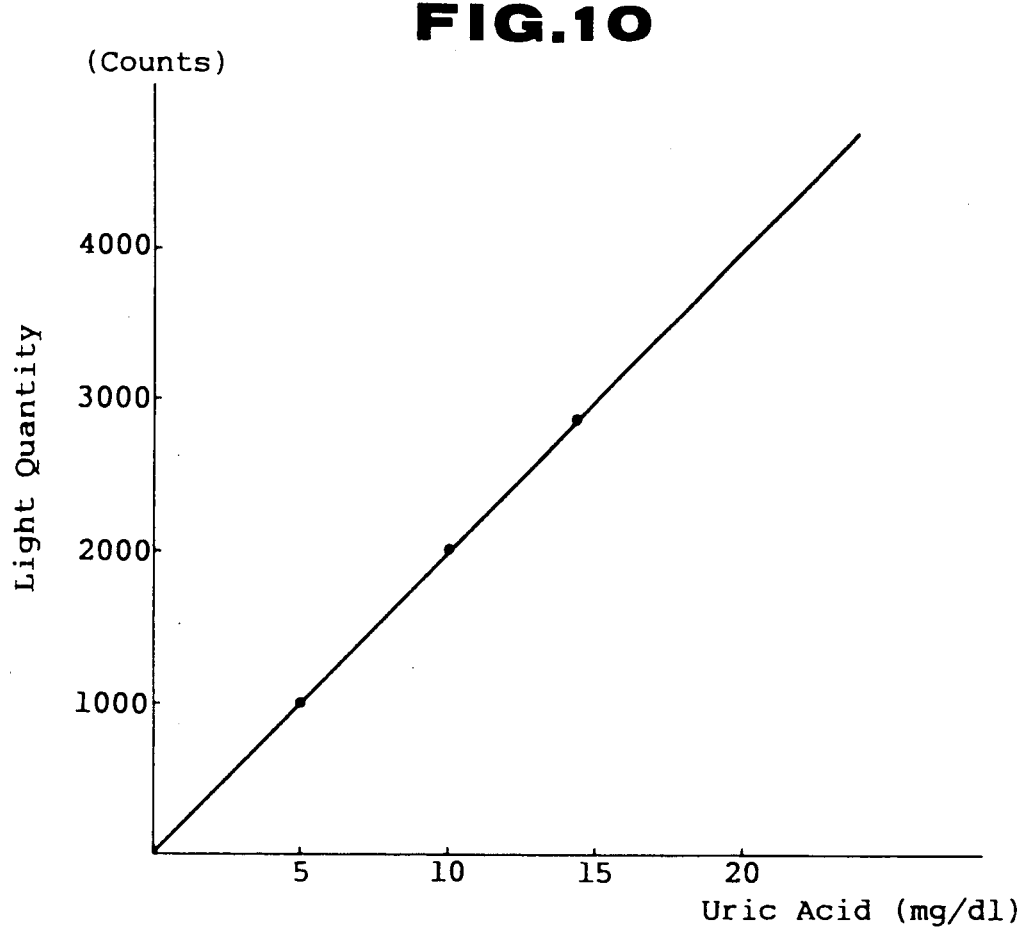
FIG. 10 is a graph illustrating the quantity of light produced versus the concentration of uric acid in uric acid containing water solution.
Figure 11:
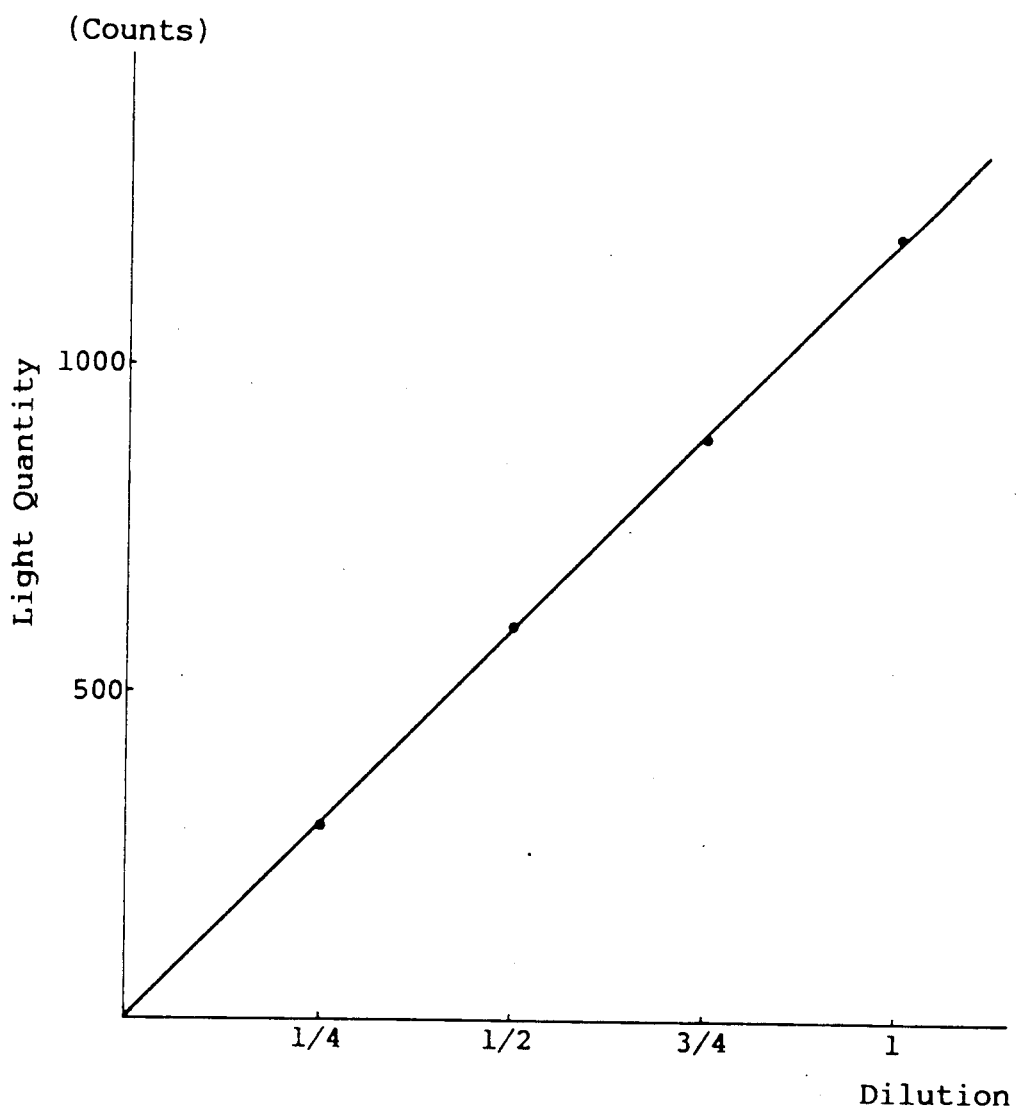
FIG. 11 is a graph illustrating the quantity of light produced versus the concentration of uric acid in Example V.

FIG. 9 is a flow chart of the aforementioned operation, FIG. 10 is a calibration curve representing the relationship between the concentrations of the uric acid in the water solutions and the quantity of light produced by the enzyme reaction, and FIG. 11 shows the relationship between the concentration of the uric acid in the urine solution and the quantity of light produced by the enzyme reaction.

As seen from FIG. 11, in the case of Example V, the quantity of light is proportional to the concentration of the uric acid. This result corresponds with that of the water solution shown in FIG. 10. Therefore, it can be shown that the low concentrations of uric acid can be accurately measured using the process of the present invention.

EXAMPLE VI

An initial urine solution containing 5.9 miligram/deciliter uric acid was prepared by adding uric acid to urine. Using this initial solution, four urine solutions were prepared in which the initial solution was undiluted, diluted with urine by a quarter, a half and three quarters.

Then, an equal volume of a buffer solution containing a 0.1 mol/liter of phosphoric acid was added to each of urine solutions, and the pH of each of the solutions was adjusted to be 7.0. Then, 2 mililiters of each of these solutions was cause to pass through the columun in which the immobilized catalase prepared in Example III was packed. To one part by volume of each of the filtrates was then added 99 parts by volume of distilled water. Thereafter, 0.01 mililiter of uricase solution prepared in Example V was added to 1 mililiter of the respective filtrates by means of pipette and the reaction therebetween was allowed to occur for ten minute at 30° C. so that hydrogen peroxide was produced. After the reaction, 0.5 mililiters of the $2 \times 10^{-7}$ mol/liter luminol solution and 0.5 mililiters of the $6 \times 10^{-3}$ mol/liter potassium ferricyanide solution, which were prepared in Example I, were added to the respective solutions. The quantity of light produced by the reaction between the luminol and the hydrogen peroxide in the presence of the potassium ferricyanide in the respective solutions was measured by luminometer.

For reference, water solutions containing 5, 10 and 14 miligram/deciliter uric acid were prepared. The quantity of light produced by each of the respective reactions in these solutions was measured in a similar manner to Example VI.

Figure 12:
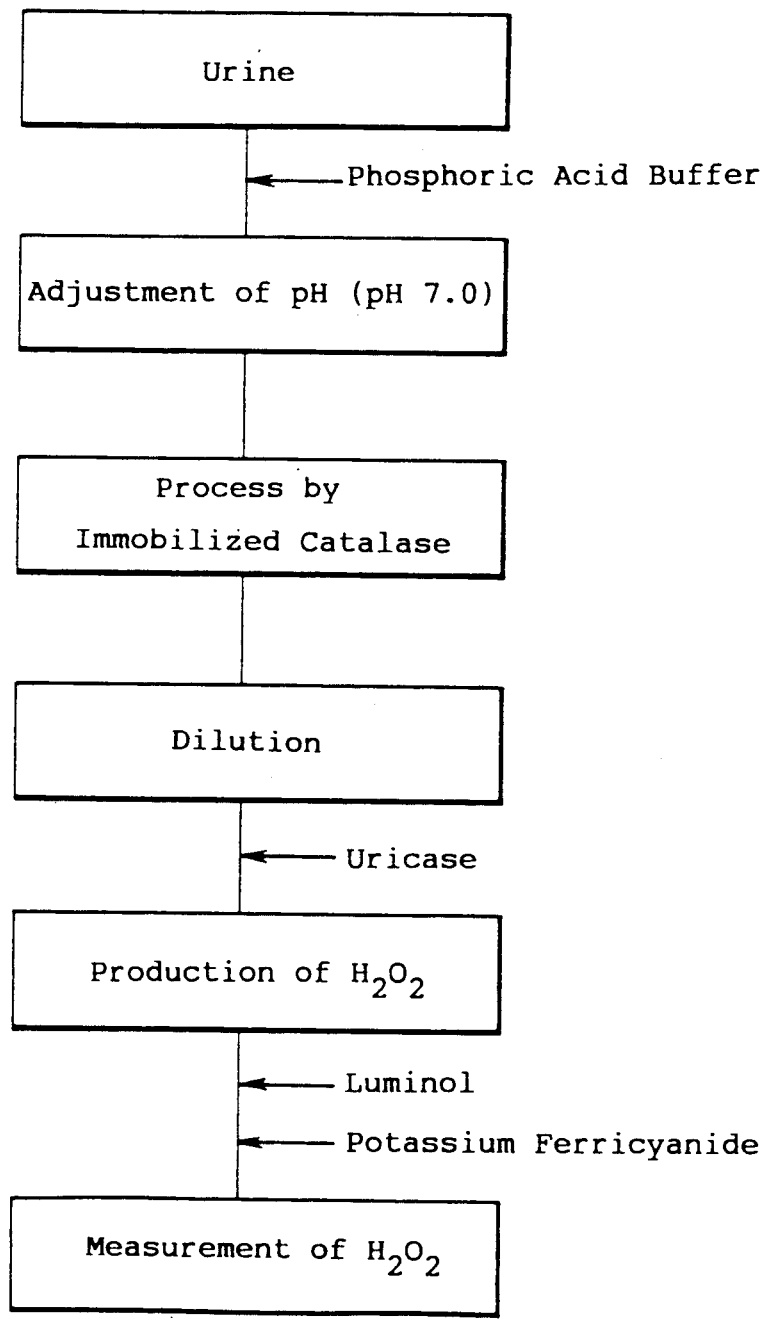
FIG. 12 is a flow chart of operations of Example VI according to the present invention.
Figure 13:
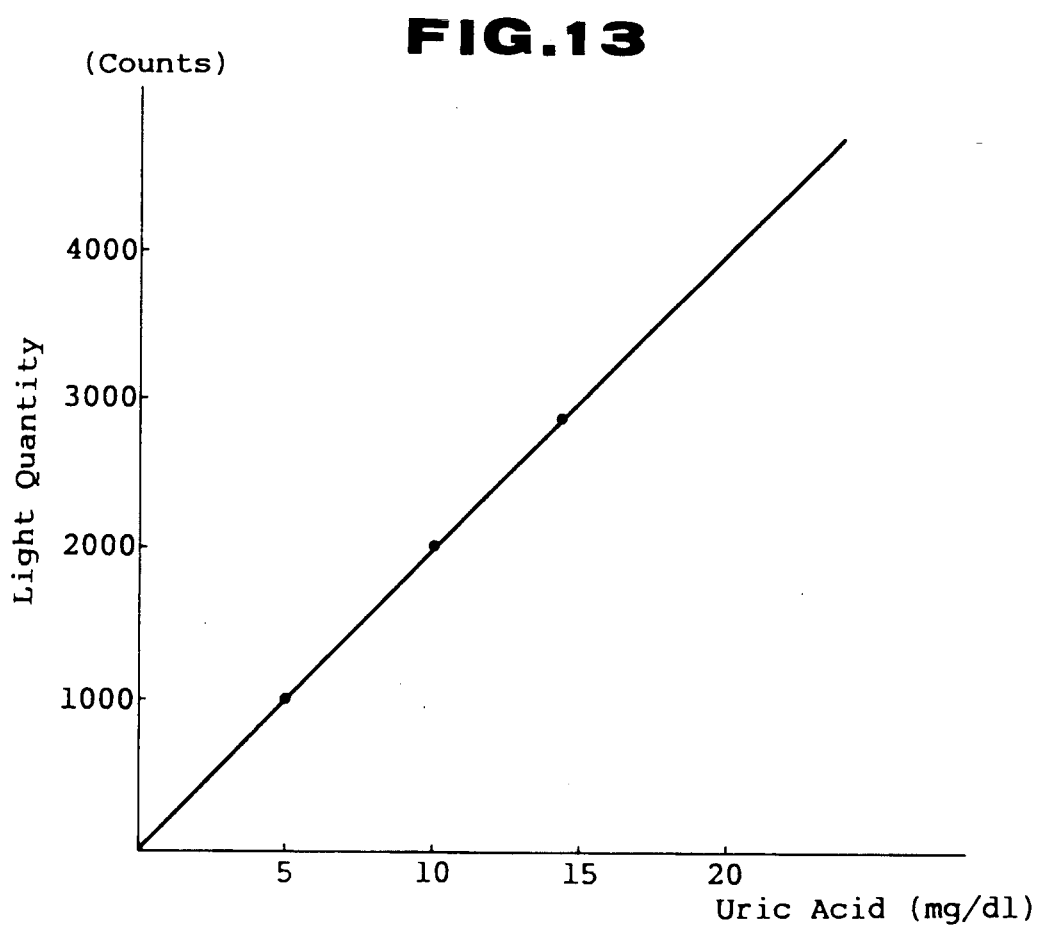
FIG. 13 is a graph illustrating the quantity of light produced versus the concentration of uric acid in uric acid containing water solution.
Figure 14:
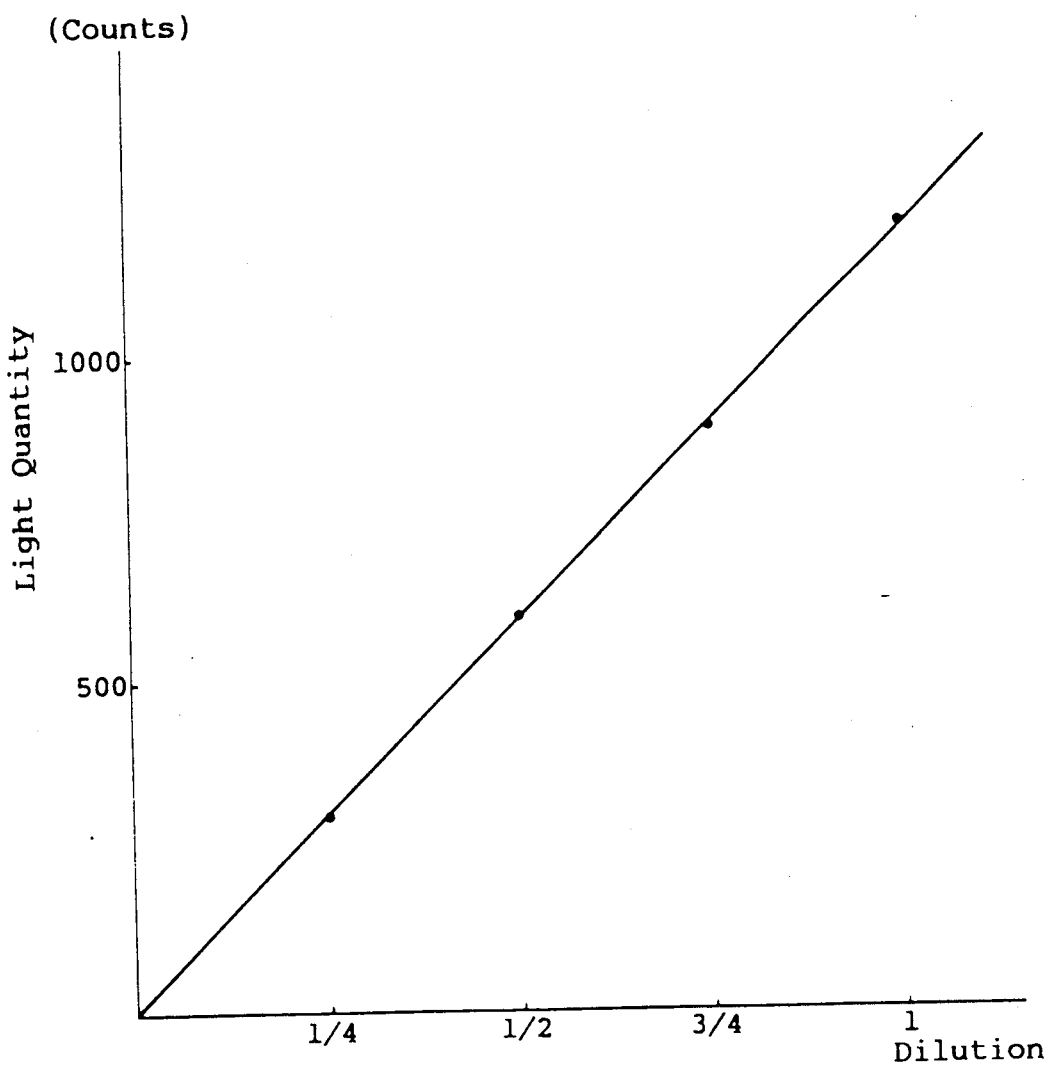
FIG. 14 is a graph illustrating the quantity of light produced versus the concentration of uric acid in Example VI.

FIG. 12 is a flow chart of the aforementioned operation, FIG. 13 is a calibration curve representing the relationship between the concentration of the uric acid in the water solution and the quantity of light produced by the enzyme reaction, and FIGS. 13 shows the relationship between the concentration of the uric acid in the urine solution and the quantity of light by the enzyme reaction.

As seen from FIGS. 12 and 13, in the case of Example VI, similar results to Example V were obtained. In accordance with this process, it is not required to use an inhibitor to inhibit the reaction between the catalase and hydrogen peroxide, so that the operation may be simpler than that of Example V if the column in which the immobilized catalase is packed is previously prepared.

EXAMPLE VII

Urine solutions containing 0, $2 \times 10^{-7}$, $2 \times 10^{-6}$, $2 \times 10^{-5}$, $2 \times 10^{-4}$, $2 \times 10^{-3}$, and $2 \times 10^{-2}$ mol/liter polyamine were prepared by adding polyamine to urine of a healthy person. Using the respective urine solutions, the following experiment was performed.

2 mililiters of strongly basic anion exchange resin similar to that of Example II was added to 2 mililiters of the urine solution, and was stirred. Then, the supernatant solution was collected, and 1 mililiter of a buffer solution (pH 8.0) containing 0.4 mol/liter tris(hydroxymethyl)-aminomethane and hydrochloric acid, which will be hereafter referred to as "TRIS-hydrochloric acid solution", and 1 mililiter of a deacetylation enzyme solution, which consists of deacetylation enzyme (acyl-polyamineamido hydrolysis enzyme made by Tokuyama Soda Co., Ltd.) dissolved in a buffer solution (pH 7.2) containing 0.1 mol/liter phosphoric acid, were added to the supernatant solution. The solution was stirred and allowed to stand in a 37° C. water bath for one hour.

After taking it out of the water bath, 1 mililiter of a buffer solution (pH 5.9) containing a 0.5 mol/liter of phosphoric acid was added to 3 mililiters of the solution, and the pH thereof was adjusted to be 7.0. Then, 0.01 mililiter of a 10,000 U/mililiter catalase prepared in Example I was added to the adjusted solution, and was allowed to warm in a 30° C. water bath for ten minutes.

After taking it out of the water bath, 0.01 mililiter of a water solution containing 1 mol/liter sodium azide similar to that of Example I, serving as the inhibitor, was added to the aforementioned solution so as to inhibit the reaction between the catalase and the hydrogen peroxide. Then, 0.4 mililiters of this solution was diluted with 0.6 mililiters water.

By the aforementioned operations, processed urine solutions essentially containing 0, $10^{-8}$, $10^{-7}$, $10^{-6}$, $10^{-5}$, $10^{-4}$ and $10^{-3}$ mol/liter polyamine were prepared. Then, 0.02 mililiters of a 10 U/mililiter putrescene oxidase solution, which was prepared by disolving putrescene oxidase (made by Tokuyama Soda Co., Ltd) in a buffer solution containing 0.1 mol/liter tris(hydroxymethyl)-aminomethane and hydrochloric acid, was added to the respective processed urine solutions, so as to cause hydrogen peroxide to be produced.

Thereafter, 0.5 mililiters of the $2 \times 10^{-7}$ mol/liter luminol solution and 0.5 mililiters of the $6 \times 10^{-3}$ mol/liter potassium ferricyanide solution, which were prepared in Example I, were added to the respective solution. The quantity of light produced by each of the reactions between the luminol and the hydrogen peroxide in the presence of the potassium ferricyanide was measured by the luminometer.

For reference, water solutions containing 0 and $10^{-8}$ to $10^{-3}$ mol/liter polyamine, and urine solutions containing 0 and $10^{-8}$ to $10^{-3}$ mol/liter polyamine, which were not processed by the catalase, the deacetylation enzyme and the strongly basic anion exchange resin, were prepared. The quantity of light produced by reaction in each of the respective reactions was measured in a similar manner to Example VII.

Figure 15:
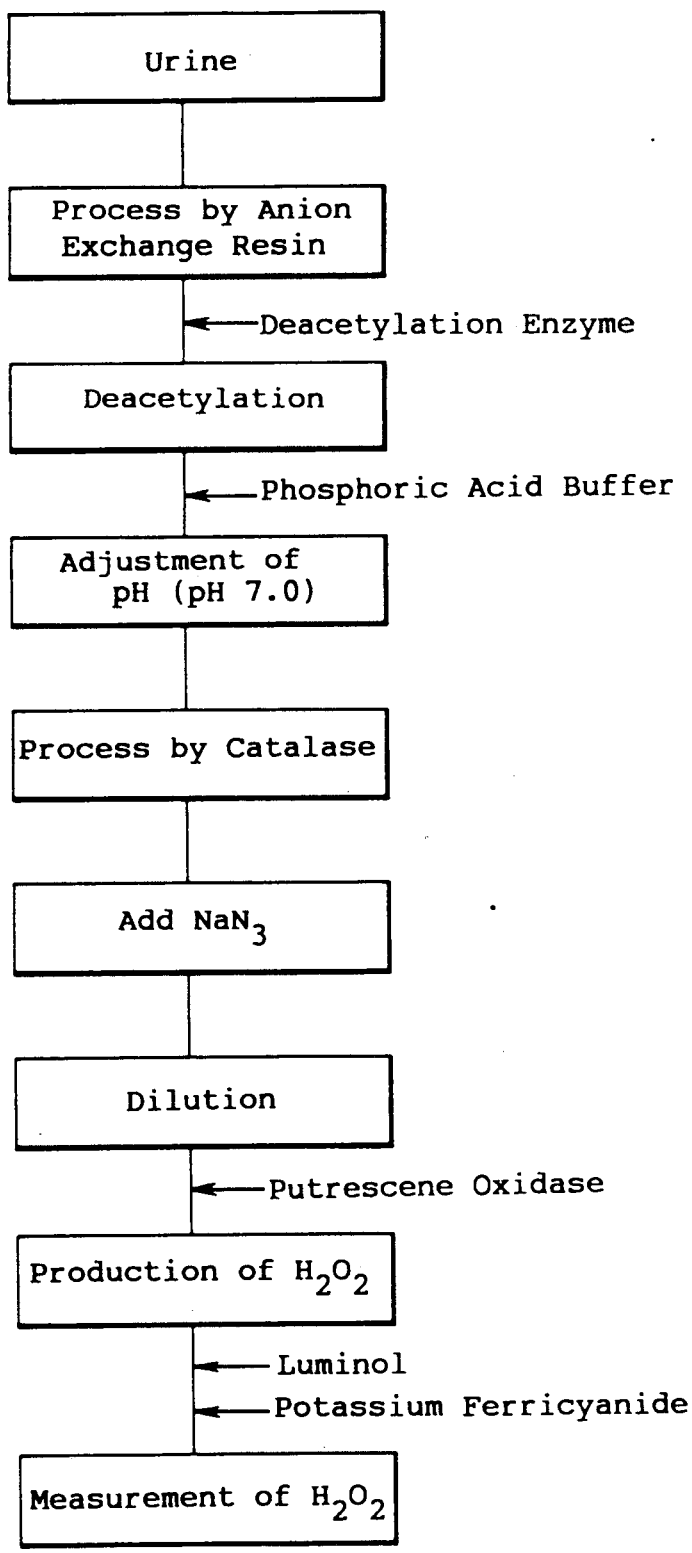
FIG. 15 is a flow chart of operations of Example VII according to the present invention.
Figure 16:
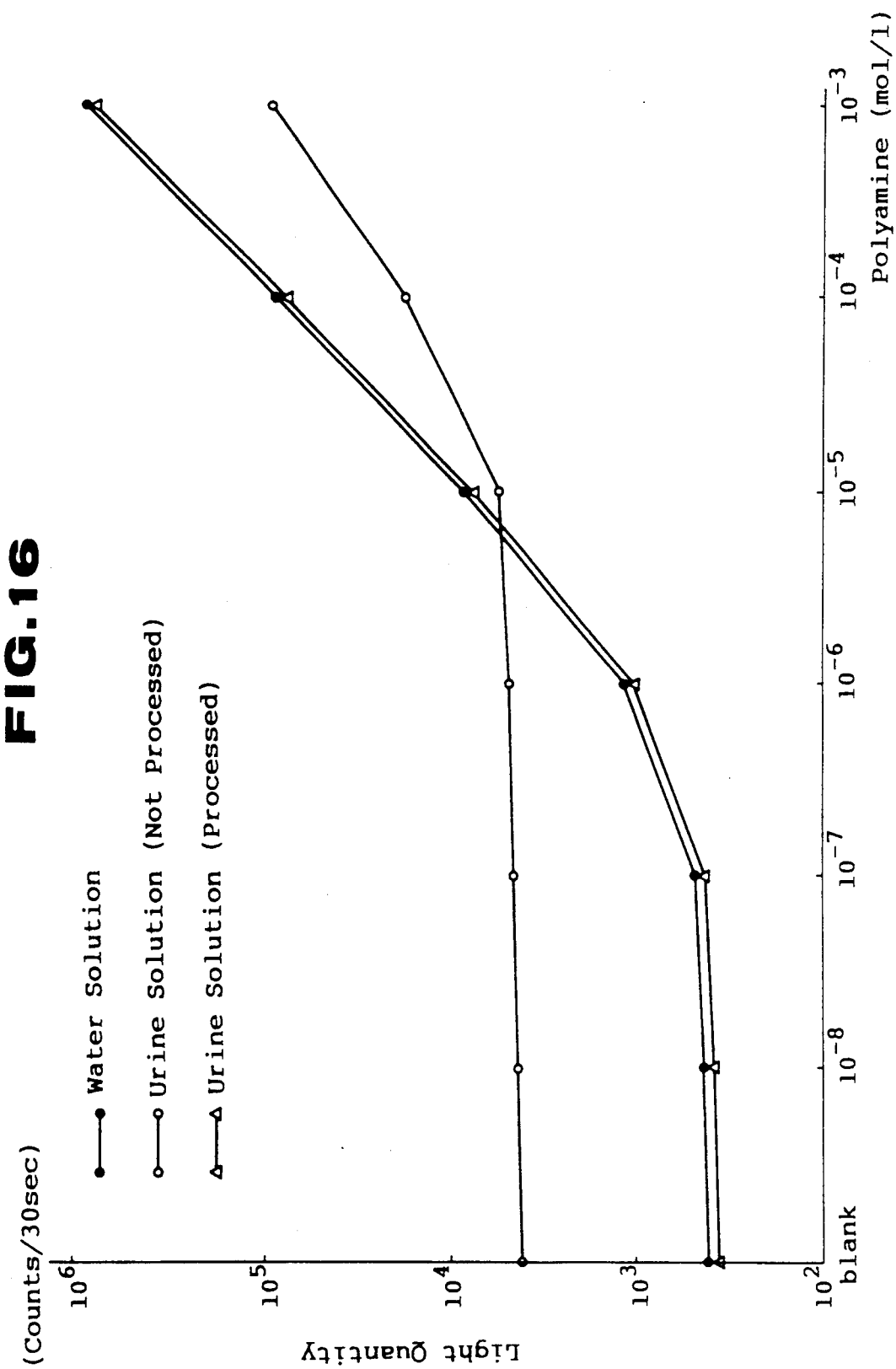
FIG. 16 is a graph illustrating the quantity of light produced versus the concentration of polyamine in Example VII.

These operations and their results are shown in FIGS. 15 and 16.

As shown in FIG. 16, in the case of urine solutions which were not processed by the catalase, the deacetylation enzyme and the strongly basic anion exchange resin, the proportion of the hydrogen peroxide included in the initial urine to the hydrogen peroxide produced by the reaction between the polyamine and the putrescene oxidase is relatively high when the concentration of polyamine is relatively low, such as $10^{-5}$ mol/liter. As a result, over all the quantity of emitted light is much greater than that of light emitted due to the hydrogen peroxide produced by the enzyme reaction. That is, the background light greatly affects the measured value when the concentration of polyamine is less than $10^{-5}$ mol/liter. On the other hand, in the case of Example VII, the background light hardly affected the measured value when the concentration of polyamine was about $10^{-8}$ mol/liter. Therefore, it was found that, according to the present invention, the concentration of polyamine can be accurately measured even when it is low, such as about $10^{-8}$ mol/liter.

EXAMPLE VIII

Urine solutions containing 0, $2.5 \times 10^{-7}$, $2.5 \times 10^{-6}$, $2.5 \times 10^{-5}$, $2.5 \times 10^{-4}$, $2.5 \times 10^{-3}$ and $2.5 \times 10^{-2}$ mol/liter polyamine were prepared by adding polyamine to urine of a healthy person. Using the respective urine solutions, the following experiment was performed.

1 mililiter of a 0.4 mol/liter of the TRIS-hydrochloric acid solution and 1 mililiter of the deacetylation enzyme solution, which were prepared in Example VII, were added to 1 mililiter of the urine solution, and were stirred. The mixture was then allowed to stand in a 37° C. water bath for one hour.

After taking it out of the water bath, 2 mililiters of the strongly basic anion exchange resin similar to that of Example II was added to 3 mililiters of the deacetylated urine, and was stirred. Then, the supernatant was collected, and 1 mililiter of a buffer solution (pH 5.9) containing a 0.5 mol/liter phosphoric acid was added to 1 mililiter of the supernatant, so that the pH thereof was adjusted to be 7.0.

This solution was caused to pass through a column in which the immobilized catalase prepared in Example III was packed, the initial 0.5 mililiters of filtrate was discarded and thereafter the filtrate was collected. Then, 0.4 mililiters of this filtrate was diluted with 0.6 mililiters water.

By the aforementioned operations, processed urine solutions essentially containing 0, $10^{-8}$, $10^{-7}$, $10^{-6}$, $10^{-5}$, $10^{-4}$ and $10^{-3}$ mol/liter polyamine were prepared. Then, 0.02 mililiters of the 10 U/mililiter putrescene oxidase solution prepared in Example VII was added to the respective processed solutions, so as to cause hydrogen peroxide to be produced.

Thereafter, 0.5 mililiters of the $2 \times 10^{-7}$ mol/liter luminol solution and 0.5 mililiters of the $6 \times 10^{-3}$ mol/liter potassium ferricyanide solution, which were prepared in Example I, were added to the aforementioned solution. The quantity of light produced by the reaction between the luminol and the hydrogen peroxide in the presence of the potassium ferricyanide was measured by luminometer.

For reference, water solutions containing 0 and $10^{-8}$ to $10^{-3}$ mol/liter polyamine, and urine solutions containing 0 and $10^{-8}$ to $10^{-3}$ mol/liter polyamine, which were not processed by the catalase, the deacetylation enzyme and the strongly basic anion exchange resin, were prepared. The quantity of light produced by the reaction in each of the respective solutions was measured in a similar manner to Example VIII.

Figure 17:
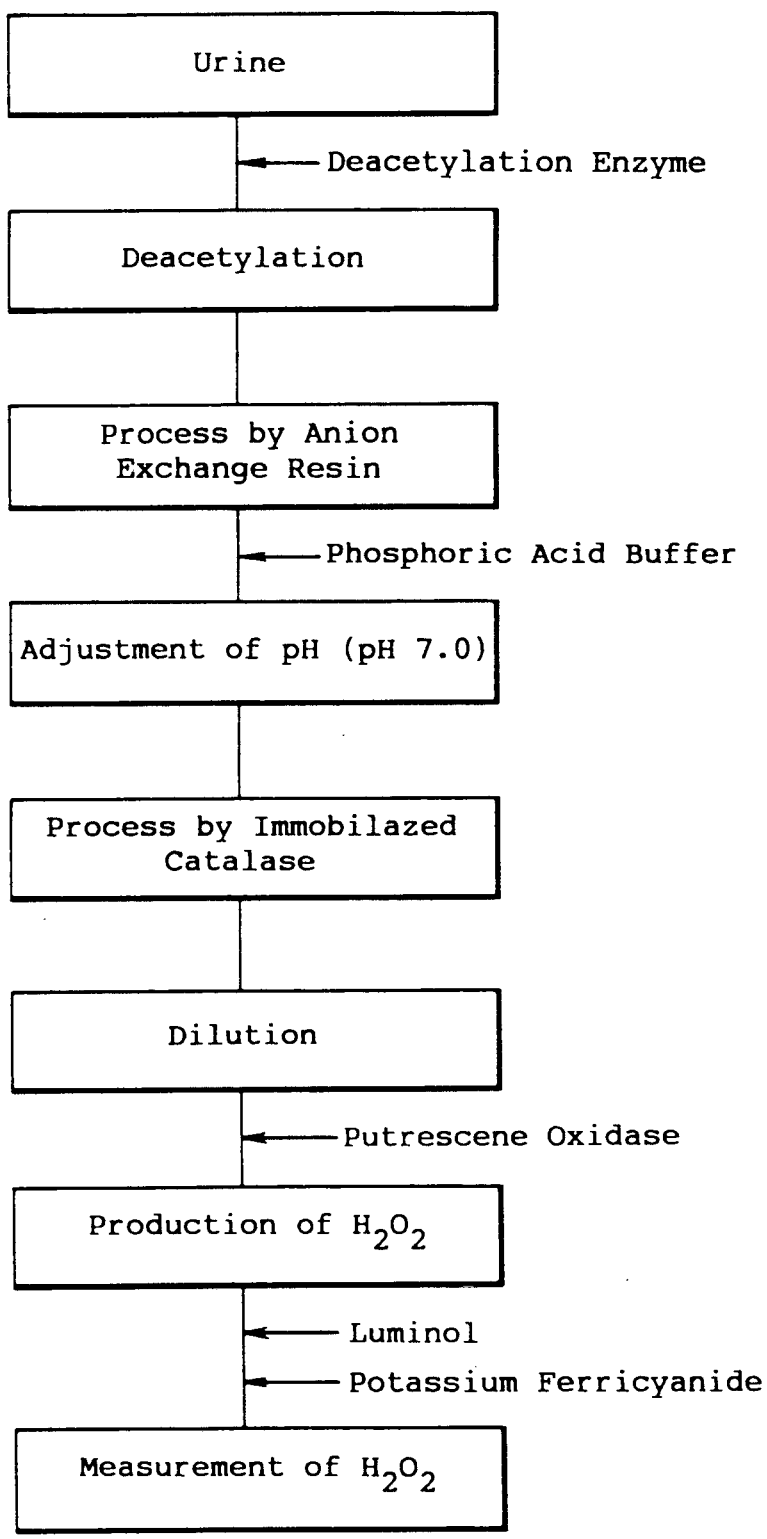
FIG. 17 is a flow chart of operations of Example VIII according to the present invention.

These operations and results are shown in FIGS. 17 and 18.

As shown in FIG. 18, in the case of Example VIII, similar results to Example VII were obtained. In accordance with this process, it is not required to use an inhibitor to inhibit the reaction between the catalase and the hydrogen peroxide, so that the operation may be simpler than that of Example VI if the column in which the immobilized catalase is packed is previously concentration.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments and modifications to the shown embodiments which can be embodied without departing from the principle of the invention set out in the appended claims.

What is claimed is:

1. A process for the determination of the concentration of a component, which selectively reacts with an oxidase to produce hydrogen peroxide, in a body fluid comprising the steps of:
   providing a body fluid;
   processing the body fluid with a strongly basic anion exchange resin to remove metabolites present in the body fluid;
   mixing the processed body fluid with a catalase for decomposing the hydrogen peroxide in the body fluid;
   adding an inhibitor, which inhibits a reaction between catalase and hydrogen peroxide, to the mixture of the catalase and the processed body fluid;
   reacting said mixture with an oxidase for producing hydrogen peroxide;
   measuring the concentration of the hydrogen peroxide produced by the reaction between said oxidase and said component; and
   determining the concentration of said component from the measured concentration of said hydrogen peroxide.

2. A process as set forth in claim 1, wherein said inhibitor is selected from the group consisting of sodium azide, hydrogen cyanide, hydrogen sulfide, ammonium hydroxide, and 3-amino-1,2,4-triazole.

3. A process as set forth in claim 1, wherein said body fluid is selected from the group consisting of urine, blood, blood serum, blood plasma, saliva, lymph and gastric juice.

4. A process as set forth in claim 1, wherein said component is selected from the group consisting of glucose, uric acid and polyamine.

5. A process as set forth in claim 1, wherein said component is glucose, and said oxidase is glucose oxidase.

6. A process as set forth in claim 1, wherein said component is uric acid, and said oxidase is uricase.

7. A process as set forth in claim 1, wherein said component is polyamine, and said oxidase is putrescene oxidase.

8. A process as set forth in claim 7, which further includes processing said body fluid with a deacetylating enzyme for converting acetylpolyamine included in said body fluid into polyamine.

9. A process as set forth in claim 8, wherein said deacetylating enzyme is acylpolyamineamido hydrolysis enzyme.

10. A process for the determination of the concentration of a component, which selectively reacts with an oxidase to produce hydrogen peroxide, in a body fluid comprising the steps of:

providing a body fluid;

processing the body fluid with a strongly basic anion exchange resin to remove metabolites present in the body fluid;

bringing said processed body fluid into contact with an immobilized catalase to decompose the hydrogen peroxide in the body fluid, and then, separating said processed body fluid from the immobilized catalase;

reacting said separated body fluid with an oxidase for producing hydrogen peroxide;

measuring the concentration of the hydrogen peroxide produced by the reaction between said oxidase and said component; and determining the concentration of said component from the measured concentration of hydrogen peroxide.

11. A process as set forth in claim 10, wherein said body fluid is selected from the group consisting of urine, blood, blood serum, blood plasma, saliva, lymph and gastric juice.

12. A process as set forth in claim 10, wherein said component is selected from the group consisting of glucose, uric acid and polyamine.

13. A process as set forth in claim 10, wherein said component is glucose, and said oxidase is glucose oxidase.

14. A process as set forth in claim 10, wherein said component is uric acid, and said oxidase is uricase.

15. A process as set forth in claim 10, wherein said component is polyamine, and said oxidase is putrescene oxidase.

16. A process as set forth in claim 15, which further includes processing said body fluid with a deacetylating enzyme for converting acetylpolyamine included in said body fluid into polyamine.

17. A process as set forth in claim 16, wherein said deacetylating enzyme is acylpolyamineamido hydrolysis enzyme.

18. A process for the determination of the concentration of a component, which selectively reacts with an oxidase to produce hydrogen peroxide, in a body fluid comprising the steps of:

providing a body fluid;

processing the body fluid with a strongly basic anion exchange resin to remove metabolites present in the body fluid;

reacting the processed body fluid with an enzyme which decomposes hydrogen peroxide, for decomposing the hydrogen peroxide therein, and then, separating the processed body fluid from the enzyme;

reacting said separated body fluid with said oxidase for producing hydrogen peroxide;

measuring the concentration of the hydrogen peroxide produced by the reaction between the oxidase and the component; and determining the concentration of said component from the measured concentration of hydrogen peroxide.

* * * * *